United States Patent
Coleman et al.

(10) Patent No.: US 8,618,102 B2
(45) Date of Patent: Dec. 31, 2013

(54) BRIDGED DIAZEPAN OREXIN RECEPTOR ANTAGONISTS

(75) Inventors: Paul J. Coleman, Harleysville, PA (US); Christopher D. Cox, Harleysville, PA (US); Georgia B. McGaughey, Harleysville, PA (US); Anthony J. Roecker, North Wales, PA (US); John D. Schreier, Red Hill, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 737 days.

(21) Appl. No.: 12/309,243

(22) PCT Filed: Jul. 13, 2007

(86) PCT No.: PCT/US2007/016037
§ 371 (c)(1),
(2), (4) Date: Jan. 9, 2009

(87) PCT Pub. No.: WO2008/008517
PCT Pub. Date: Jan. 17, 2008

(65) Prior Publication Data
US 2009/0239843 A1    Sep. 24, 2009

Related U.S. Application Data

(60) Provisional application No. 60/831,178, filed on Jul. 14, 2006.

(51) Int. Cl.
*A61P 3/04* (2006.01)
*A61K 31/44* (2006.01)
*C07D 471/08* (2006.01)

(52) U.S. Cl.
USPC . 514/249; 514/255.05; 514/256; 514/266.21; 514/300; 514/302; 544/284; 544/328; 544/356; 544/405; 546/300; 546/302

(58) Field of Classification Search
USPC ............... 514/249, 255.05, 256, 266.21, 300, 514/302; 544/284, 328, 356, 405; 546/300, 546/302
See application file for complete search history.

(56) References Cited

U.S. PATENT DOCUMENTS

| | | | |
|---|---|---|---|
| 6,153,608 | A | 11/2000 | Hidaka et al. |
| 6,440,970 | B1 | 8/2002 | Clark et al. |
| 2003/0225268 | A1 | 12/2003 | Bunnelle et al. |
| 2003/0225368 | A1 | 12/2003 | Bunelle et al. |
| 2005/0065178 | A1 | 3/2005 | Basha et al. |
| 2005/0101602 | A1 | 5/2005 | Bunnelle et al. |
| 2008/0132490 | A1 | 6/2008 | Bergman et al. |

FOREIGN PATENT DOCUMENTS

| | | |
|---|---|---|
| EP | 0885888 | 12/1998 |
| WO | WO00/044755 | 8/2000 |
| WO | WO 2007/126935 | 11/2007 |
| WO | WO 2008/008518 | 1/2008 |
| WO | WO 2008/143856 | 11/2008 |

OTHER PUBLICATIONS

International Search Report for WO 2008/008517 (Sep. 26, 2008).
International Search Report for WO 2008/008517 (Jan. 14, 2009).
Supplementary European Search Report and European Search Opinion for EP 2049110 (Jul. 13, 2011).

*Primary Examiner* — Brenda Coleman
(74) *Attorney, Agent, or Firm* — J. Eric Thies; John C. Todaro

(57) ABSTRACT

The present invention is directed to bridged diazepan compounds which are antagonists of orexin receptors, and which are useful in the treatment or prevention of neurological and psychiatric disorders and diseases in which orexin receptors are involved. The invention is also directed to pharmaceutical compositions comprising these compounds and the use of these compounds and compositions in the prevention or treatment of such diseases in which orexin receptors are involved.

12 Claims, No Drawings

BRIDGED DIAZEPAN OREXIN RECEPTOR ANTAGONISTS

CROSS REFERENCE TO RELATED APPLICATIONS

This application is a U.S. National Phase application under 35 U.S.C. §371 of PCT Application No. PCT/US2007/016037 filed Jul. 13, 2007, which claims priority under 35 U.S.C. §119 from U.S. Application No. 60/831,178, filed Jul. 14, 2006.

BACKGROUND OF THE INVENTION

The orexins (hypocretins) comprise two neuropeptides produced in the hypothalamus: the orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behaviour (Sakurai T. et al., Cell, 1998, 92, 573-585). Orexins also regulate states of sleep and wakefulness opening potentially novel therapeutic approaches for narcoleptic or insomniac patients (Chemelli R. M. et al., Cell, 1999, 98, 437-451). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A and the orexin-2 receptor (OX2 or OX2R) is capable to bind OX-A as well as OX-B. The physiological actions in which orexins are presumed to participate are thought to be expressed via one or both of OX 1 receptor and OX 2 receptor as the two subtypes of orexin receptors.

Orexin receptors are found in the mammalian brain and may have numerous implications in pathologies such as depression; anxiety; addictions; obsessive compulsive disorder; affective neurosis; depressive neurosis; anxiety neurosis; dysthymic disorder; behaviour disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders such as anorexia, bulimia, cachexia, and obesity; addictive feeding behaviors; binge/purge feeding behaviors; cardiovascular diseases; diabetes; appetite/taste disorders; emesis, vomiting, nausea; asthma; cancer; Parkinson's disease; Cushing's syndrome/disease; basophile adenoma; prolactinoma; hyperprolactinemia; hypophysis tumour/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; conditions associated with visceral pain such as irritable bowel syndrome, and angina; migraine; urinary bladder incontinence e.g. urge incontinence; tolerance to narcotics or withdrawal from narcotics; sleep disorders; sleep apnea; narcolepsy; insomnia; parasomnia; jet lag syndrome; and neurodegenerative disorders including nosological entities such as disinhibition-dementia-parkinsonism-amyotrophy complex; pallido-ponto-nigral degeneration; epilepsy; seizure disorders and other diseases related to general orexin system dysfunction.

Certain orexin receptor antagonists are disclosed in PCT patent publications WO 99/09024, WO 99/58533, WO 00/47576, WO 00/47577, WO 00/47580, WO 01/68609, WO 01/85693, WO 01/96302, WO 2002/044172, WO 2002/051232, WO 2002/051838, WO 2002/089800, WO 2002/090355, WO 2003/002559, WO 2003/002561, WO 2003/032991, WO 2003/037847, WO 2003/041711, WO 2003/051368, WO 2003/051872, WO 2003/051873, WO 2004/004733, WO 2004/026866, WO 2004/033418, WO 2004/041807, WO 2004/041816, WO 2004/052876, WO 2004/083218, WO 2004/085403, WO 2004/096780, WO 2005/060959, WO 2005/075458, WO2005/118548, WO 2006/067224, WO 2006/110626, WO 2006/127550, WO 2007/019234 and WO 2007/025069.

SUMMARY OF THE INVENTION

The present invention is directed to diazepan compounds which are antagonists of orexin receptors, and which are useful in the treatment or prevention of neurological and psychiatric disorders and diseases in which orexin receptors are involved. The invention is also directed to pharmaceutical compositions comprising these compounds and the use of these compounds and compositions in the prevention or treatment of such diseases in which orexin receptors are involved.

DETAILED DESCRIPTION OF THE INVENTION

The present invention is directed to compounds of the formula I:

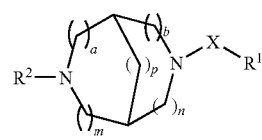

wherein:
a is 0 or 1, b is 0 or 1, m is 0 or 1, and n is 0 or 1, wherein the sum of a+b+m+n=3;
p is 1 or 2;
X is selected from —SO$_2$—, —(C=O)—, and —(C=S)—;
R$^1$ is selected from the group consisting of:
 (1) phenyl, where the phenyl is substituted with R$^{1a}$, R$^{1b}$ and R$^{1c}$,
 (2) napthyl, where the napthyl is substituted with R$^{1a}$, R$^{1b}$ and R$^{1c}$, and
 (3) heteroaryl, where the heteroaryl is substituted with R$^{1a}$, $R^{1b}$ and $R^{1c}$;
$R^2$ is heteroaryl, where the heteroaryl is substituted with $R^{2a}$, $R^{2b}$ and $R^{2c}$;
$R^{1a}$, $R^{1b}$, $R^{1c}$, $R^{2a}$, $R^{2b}$ and $R^{2c}$ are independently selected from the group consisting of:
(1) hydrogen,
(2) halogen,
(3) hydroxyl,
(4) $-(C=O)_m-O_n-C_{1-6}$alkyl, where m is 0 or 1, n is 0 or 1 (wherein if m is 0 or n is 0, a bond is present) and where the alkyl is unsubstituted or substituted with one or more substituents selected from $R^{13}$,
(5) $-(C=O)_m-O_n-C_{3-6}$cycloalkyl, where the cycloalkyl is unsubstituted or substituted with one or more substituents selected from $R^{13}$,
(6) $-(C=O)_m-C_{2-4}$alkenyl, where the alkenyl is unsubstituted or substituted with one or more substituents selected from $R^{13}$,
(7) $-(C=O)_m-C_{2-4}$alkynyl, where the alkynyl is unsubstituted or substituted with one or more substituents selected from $R^{13}$,
(8) $-(C=O)_m-O_n$-phenyl or $-(C=O)_m-O_n$-napthyl, where the phenyl or napthyl is unsubstituted or substituted with one or more substituents selected from $R^{13}$,
(9) $-(C=O)_m-O_n$-heterocycle, where the heterocycle is unsubstituted or substituted with one or more substituents selected from $R^{13}$,
(10) $-(C=O)_m-NR^{10}R^{11}$, wherein $R^{10}$ and $R^{11}$ are independently selected from the group consisting of:
(a) hydrogen,
(b) $C_{1-6}$alkyl, which is unsubstituted or substituted with one or more substituents selected from $R^{13}$,
(c) $C_{3-6}$alkenyl, which is unsubstituted or substituted with one or more substituents selected from $R^{13}$,
(d) cycloalkyl, which is unsubstituted or substituted with one or more substituents selected from $R^{13}$,
(e) phenyl, which is unsubstituted or substituted with one or more substituents selected from $R^{13}$, and
(f) heterocycle, which is unsubstituted or substituted with one or more substituents selected from $R^{13}$,
(11) $-S(O)_2-NR^{10}R^{11}$,
(12) $-S(O)_q-R^{12}$, where q is 0, 1 or 2 and where $R^{12}$ is selected from the definitions of $R^{10}$ and $R^{11}$,
(13) $-CO_2H$,
(14) $-CN$, and
(15) $-NO_2$;
$R^{13}$ is selected from the group consisting of:
(1) halogen,
(2) hydroxyl,
(3) $-(C=O)_m-O_n-C_{1-6}$alkyl, where the alkyl is unsubstituted or substituted with one or more substituents selected from $R^{14}$,
(4) $-O_n-(C_{1-3})$perfluoroalkyl,
(5) $-(C=O)_m-O_n-C_{3-6}$cycloalkyl, where the cycloalkyl is unsubstituted or substituted with one or more substituents selected from $R^{14}$,
(6) $-(C=O)_m-C_{2-4}$alkenyl, where the alkenyl is unsubstituted or substituted with one or more substituents selected from $R^{14}$,
(7) $-(C=O)_m-O_n$-phenyl or $-(C=O)_m-O_n$-napthyl, where the phenyl or napthyl is unsubstituted or substituted with one or more substituents selected from $R^{14}$,
(8) $-(C=O)_m-O_n$-heterocycle, where the heterocycle is unsubstituted or substituted with one or more substituents selected from $R^{14}$,
(9) $-(C=O)_m-NR^{10}R^{11}$,
(10) $-S(O)_2-NR^{10}R^{11}$,
(11) $-S(O)_q-R^{12}$,
(12) $-CO_2H$,
(13) $-CN$, and
(14) $-NO_2$;
$R^{14}$ is selected from the group consisting of:
(1) hydroxyl,
(2) halogen,
(3) $C_{1-6}$alkyl,
(4) $-C_{3-6}$cycloalkyl,
(5) $-O-C_{1-6}$alkyl,
(6) $-O(C=O)-C_{1-6}$alkyl,
(7) $-NH-C_{1-6}$alkyl,
(8) phenyl,
(9) heterocycle,
(10) $-CO_2H$, and
(11) $-CN$;
or a pharmaceutically acceptable salt thereof.

An embodiment of the present invention includes compounds of the formula Ib:

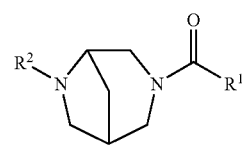

Ib wherein $R^1$ and $R^2$ are defined herein; or a pharmaceutically acceptable salt thereof.

An embodiment of the present invention includes compounds of the formula Ic:

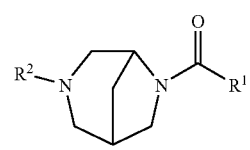

Ic wherein $R^1$ and $R^2$ are defined herein; or a pharmaceutically acceptable salt thereof.

An embodiment of the present invention includes compounds of the formula Id:

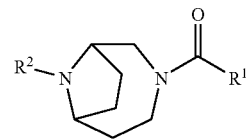

Id wherein $R^1$ and $R^2$ are defined herein; or a pharmaceutically acceptable salt thereof.

An embodiment of the present invention includes compounds of the formula Ie:

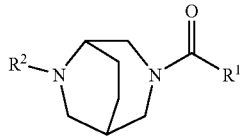

Ie wherein $R^1$ and $R^2$ are defined herein; or a pharmaceutically acceptable salt thereof.

An embodiment of the present invention includes compounds of the formula If:

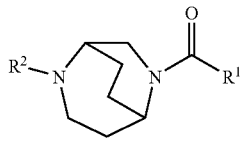

If wherein $R^1$ and $R^2$ are defined herein; or a pharmaceutically acceptable salt thereof.

An embodiment of the present invention includes compounds of the formula Ig:

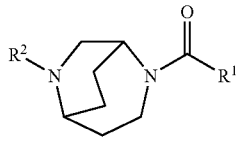

Ig wherein $R^1$ and $R^2$ are defined herein; or a pharmaceutically acceptable salt thereof.

An embodiment of the present invention includes compounds of the formula Ih:

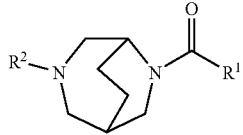

Ih wherein $R^1$ and $R^2$ are defined herein; or a pharmaceutically acceptable salt thereof.

An embodiment of the present invention includes compounds of the formula Ii:

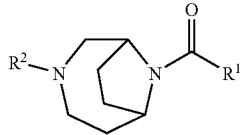

Ii wherein $R^1$ and $R^2$ are defined herein; or a pharmaceutically acceptable salt thereof.

An embodiment of the present invention includes compounds wherein
X is —SO$_2$—.

An embodiment of the present invention includes compounds wherein
X is —(C═O)—.

An embodiment of the present invention includes compounds wherein
X is —(C═S)—.

An embodiment of the present invention includes compounds wherein
$R^1$ is phenyl, which is unsubstituted or substituted with one or more of:
(1) halogen,
(2) hydroxyl,
(3) —O$_n$—C$_{1-6}$alkyl, where n is 0 or 1 (wherein if n is 0, a bond is present) and where the alkyl is unsubstituted or substituted with one or more substituents selected from $R^{13}$,
(4) —O$_n$-phenyl, where the phenyl is unsubstituted or substituted with one or more substituents selected from $R^{13}$,
(5) -heterocycle, where the heterocycle is unsubstituted or substituted with one or more substituents selected from $R^{13}$,
(6) —NR$^{10}$R$^{11}$, wherein $R^{10}$ and $R^{11}$ are independently selected from the group consisting of:
(a) hydrogen,
(b) C$_{1-6}$alkyl, which is unsubstituted or substituted with one or more substituents selected from $R^{13}$,
(7) —S(O)$_2$—NR$^{10}$R$^{11}$,
(8) —CO$_2$H,
(9) —CN, and
(10) —NO$_2$.

An embodiment of the present invention includes compounds wherein
$R^1$ is phenyl, which is unsubstituted or substituted with one or more methyl, —CF$_3$, halo, —OCF$_3$, —OCH$_3$, —OCH$_2$CH$_3$, —CO$_2$CH$_3$, —CN, —N(CH$_3$), —NH(CH$_2$CH$_3$), —NO$_2$, triazolyl or phenyl.

An embodiment of the present invention includes compounds wherein
$R^1$ is phenyl, which is unsubstituted or substituted with one or more methyl, —CF$_3$, chloro, fluoro, —OCF$_3$, —OCH$_3$, —OCH$_2$CH$_3$, —CO$_2$CH$_3$, triazolyl or phenyl.

An embodiment of the present invention includes compounds wherein
$R^1$ is phenyl, which is unsubstituted or substituted with one or more methyl, —CF$_3$, fluoro, —OCF$_3$, —OCH$_3$, —CO$_2$CH$_3$ or phenyl.

An embodiment of the present invention includes compounds wherein
$R^1$ is selected from the group consisting of:
(1) phenyl,
(2) biphenyl,
(3) 2,6-dimethoxyphenyl,
(4) 2,4-dichlorophenyl,
(5) 2,6-dichlorophenyl,
(6) 2,3-difluorophenyl,
(7) 2,4-difluorophenyl,
(8) 2,6-difluorophenyl,
(9) 2-methoxy-4-methyl-phenyl,
(10) 3-methoxy-biphenyl,
(11) 3-methyl-biphenyl, and
(12) 5-methyl-2-triazolyl-phenyl.

An embodiment of the present invention includes compounds wherein
$R^1$ is phenyl.

An embodiment of the present invention includes compounds wherein
$R^1$ is 2,6-dimethoxyphenyl.

An embodiment of the present invention includes compounds wherein
$R^2$ is heteroaryl, which is unsubstituted or substituted with one or more of:
  (1) halogen,
  (2) hydroxyl,
  (3) —$O_n$—$C_{1-6}$alkyl, where n is 0 or 1 (wherein if n is 0, a bond is present) and where the alkyl is unsubstituted or substituted with one or more substituents selected from $R^{13}$,
  (4) —$O_n$-phenyl, where the phenyl is unsubstituted or substituted with one or more substituents selected from $R^{13}$,
  (5) -heterocycle, where the heterocycle is unsubstituted or substituted with one or more substituents selected from $R^{13}$,
  (6) —$NR^{10}R^{11}$, wherein $R^{10}$ and $R^{11}$ are independently selected from the group consisting of:
    (a) hydrogen,
    (b) $C_{1-6}$alkyl, which is unsubstituted or substituted with one or more substituents selected from $R^{13}$,
  (7) —$S(O)_2$—$NR^{10}R^{13}$,
  (8) —$CO_2H$,
  (9) —CN, and
  (10) —$NO_2$.

An embodiment of the present invention includes compounds wherein
$R^2$ is heteroaryl, which is unsubstituted or substituted with halogen, hydroxyl, $C_{1-6}$alkyl, —O—$C_{1-6}$alkyl or phenyl.

An embodiment of the present invention includes compounds wherein
$R^2$ is selected from the group consisting of:
  (1) benzimidazolyl,
  (2) benzothiazolyl,
  (3) benzoxazolyl,
  (4) quinazolinyl,
  (5) quinolinyl, and
  (6) thiadiazolyl,
which is unsubstituted or substituted with halogen, hydroxyl, $C_{1-6}$alkyl, —O—$C_{1-6}$alkyl or phenyl.

An embodiment of the present invention includes compounds wherein
$R^2$ is selected from the group consisting of:
  (1) benzimidazol-2-yl,
  (2) 1,3-benzothiazol-2-yl,
  (3) 1,3-benzoxazol-2-yl,
  (4) 2-quinazolinyl,
  (5) 1-quinolin-2-yl, and
  (6) 1,2,4-thiadiazol-5-yl,
which is unsubstituted or substituted with methyl, fluoro, chloro or phenyl.

An embodiment of the present invention includes compounds wherein
$R^2$ is benzothiazolyl, which is unsubstituted or substituted with chloro.

An embodiment of the present invention includes compounds wherein
$R^2$ is 6-chloro-benzothiazolyl.

An embodiment of the present invention includes compounds wherein
$R^2$ is benzoxazolyl.

An embodiment of the present invention includes compounds wherein
$R^2$ is quinazolinyl or quinolinyl.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, and hexyl A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (i.e. "heteroaryl") include benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyrimidyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonizing orexin receptor activity in a patient such as a mammal in need of such inhibition comprising the administration of an effective amount of the compound. The present invention is directed to the use of the compounds disclosed herein as antagonists of orexin receptor activity. In addition to primates, especially humans, a variety of other mammals can be treated according to the method of the present invention. The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for antagonizing orexin receptor activity or treating the disorders and diseases noted herein in humans and animals.

The subject treated in the present methods is generally a mammal, preferably a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as orexin receptor OX1R and/or OX2R antagonists may be readily determined without undue experimentation by methodology well known in the art, including the "FLIPR $Ca^{2+}$ Flux Assay" (Okumura et al., Biochem. Biophys. Res. Comm. 280:976-981, 2001). In a typical experiment the OX1 and OX2 receptor antagonistic activity of the compounds of the present invention was determined in accordance with the following experimental method. For intracellular calcium measurements, Chinese hamster ovary (CHO) cells expressing the rat orexin-1 receptor or the human orexin-2 receptor, are grown in Iscove's modified DMEM containing 2 mM L-glutamine, 0.5 g/ml G418, 1% hypoxanthine-thymidine supplement, 100 U/ml penicillin, 100 ug/ml streptomycin and 10% heat-inactivated fetal calf serum (FCS). The cells are seeded at 20,000 cells/well into Becton-Dickinson black 384-well clear bottom sterile plates coated with poly-D-lysine. All reagents were from GIBCO-Invitrogen Corp. The seeded plates are incubated overnight at 37° C. and 5% $CO_2$. $Ala^{6,12}$ human orexin-A as the agonist is prepared as a 1 mM stock solution in 1% bovine serum albumin (BSA) and diluted in assay buffer (HBSS containing 20 mM HEPES, 0.1% BSA and 2.5 mM probenecid, pH7.4) for use in the assay at a final concentration of 70 pM. Test compounds are prepared as 10 mM stock solution in DMSO, then diluted in 384-well plates, first in DMSO, then assay buffer. On the day of the assay, cells are washed 3 times with 100 ul assay buffer and then incubated for 60 min (37° C., 5% CO2) in 60 ul assay buffer containing 1 uM Fluo-4AM ester, 0.02% pluronic acid, and 1% BSA. The dye loading solution is then aspirated and cells are washed 3 times with 100 ul assay buffer. 30 ul of that same buffer is left in each well. Within the Fluorescent Imaging Plate Reader (FLIPR, Molecular Devices), test compounds are added to the plate in a volume of 25 ul, incubated for 5 min and finally 25 ul of agonist is added. Fluorescence is measured for each well at 1 second intervals for 5 minutes and the height of each fluorescence peak is compared to the height of the fluorescence peak induced by 70 pM Ala$^{6,12}$ orexin-A with buffer in place of antagonist. For each antagonist, IC50 value (the concentration of compound needed to inhibit 50% of the agonist response) is determined. The intrinsic orexin receptor antagonist activity of a compound which may be used in the present invention may be determined by these assays.

In particular, the compounds of the following examples had activity in antagonizing the rat orexin-1 receptor and/or the human orexin-2 receptor in the aforementioned assays, generally with an $IC_{50}$ of less than about 50 µM. Preferred compounds within the present invention had activity in antagonizing the rat orexin-1 receptor and/or the human orexin-2 receptor in the aforementioned assays with an $IC_{50}$ of less than about 100 nM. Such a result is indicative of the intrinsic activity of the compounds in use as antagonists of orexin-1 receptor and/or the orexin-2 receptor. The present invention also includes compounds within the generic scope of the invention which possess activity as agonists of the orexin-1 receptor and/or the orexin-2 receptor. With respect to other diazepan compounds, the present compounds exhibit unexpected properties, such as with respect to increased oral bioavailability, metabolic stability, and/or selectivity with respect to other receptors.

The orexin receptors have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with orexin receptors, including one or more of the following conditions or diseases: sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersommia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders including overeating and bulimia nervosa, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, addictive feeding, dependence or withdrawal from substances including alcohol, amphetamines, cannabis, cocaine, hallucinogens, inhalants, nicotine, opioids, phencyclidine, sedatives, hypnotics or anxiolytics); movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); attention deficit/hyperactivity disorder (ADHD); conduct disorder; migraine (including migraine headache); urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Thus, in specific embodiments the present invention provides methods for: enhancing the quality of sleep; augmenting sleep maintenance; increasing REM sleep; increasing stage 2 sleep; decreasing fragmentation of sleep patterns; treating insomnia; enhancing cognition; increasing memory retention; treating or controlling obesity; treating or controlling depression; treating, controlling, ameliorating or reducing the risk of epilepsy, including absence epilepsy; treating or controlling pain, including neuropathic pain; treating or controlling Parkinson's disease; treating or controlling psychosis; or treating, controlling, ameliorating or reducing the risk of schizophrenia, in a mammalian patient in need thereof which comprises administering to the patient a therapeutically effective amount of a compound of the present invention.

The subject compounds are further useful in a method for the prevention, treatment, control, amelioration, or reducation of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of orexin receptors. The dosage range will generally be about 0.5 mg to 1.0 g. per patient per day which may be administered in single or multiple doses. Preferably, the dosage range will be about 0.5 mg to 500 mg per patient per day; more preferably about 0.5 mg to 200 mg per patient per day; and even more preferably about 5 mg to 50 mg per patient per day. Pharmaceutical compositions of the present invention may be provided in a solid dosage formulation preferably comprising about 0.5 mg to 500 mg active ingredient, more preferably comprising about 1 mg to 250 mg active ingredient. The pharmaceutical composition is preferably provided in a solid dosage formulation comprising about 1 mg, 5 mg, 10 mg, 25 mg, 50 mg, 100 mg, 200 mg or 250 mg active ingredient. For oral administration, the compositions are preferably provided in the form of tablets containing 1.0 to 1000 milligrams of the active ingredient, particularly 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with other compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, include, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA:cholesterol acyltransferase (ACAT)) inhibitors such as avasimibe, and melinamide, (v) anti-oxidants, such as probucol, (vi) vitamin E, and (vii) thyromirnmetics; (f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579 by Glaxo; (g) PPARδ agonists; (h) PPAR α/δ agonists, such as muraglitazar, and the compounds disclosed in U.S. Pat. No. 6,414,002; and (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255; (2) protein tyrosine phosphatase-1B (PTP-1B) inhibitors; (3) cannabinoid receptor ligands, such as cannabinoid CBI receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate; (7) neuropeptide Y1 antagonists, such as BIBP3226, J-115814, BIBO 3304, LY-357897, CP-671906, GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) other Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065; (18) galanin antagonists; (19) CCK agonists; (20) CCK-A (cholecystokinin-A) agonists, such as AR-R 15849, GI 181771, JMV-180, A-71378, A-71623 and SR14613; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (β-HSD-1); 26) PDE (phosphodiesterase) inhibitors, such as theophylline, pentoxifylline, zaprinast, sildenafil, arnrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6,beta-Ala11,Phe13,Nle14]Bn(6-14) and [D-Phe6,Phe13]Bn(6-13) propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid; (37) thyroid hormone β agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, MK-431, P93/01, TSL 225, TMC-2A/2B/2C, FE 999011, P9310/K364, VIP 0177, SDZ 274-444; (46) dicarboxylate transporter inhibitors; (47) glucose transporter inhibitors; (48) phosphate transporter inhibitors; (49) Metformin (Glucophage®); and (50) Topiramate (Topimax®); and (50) peptideYY, PYY 3-36, peptideYY analogs, derivatives, and fragments such as BIM-43073D, BIM-43004C (Olitvak, D. A. et al., Dig. Dis. Sci. 44(3):643-48 (1999)); (51) NeuropeptideY2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) NeuropeptideY4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 11β HSD-1 (11-beta hydroxy steroid dehydrogenase type 1) inhibitor such as BVT 3498, BVT 2733; (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H$_3$ antagonists; AMPA agonists; PDE IV inhibitors; GABA$_A$ inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with acetophenazine, alentemol, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In another embodiment, the subject compound may be employed in combination with an anoretic agent such as aminorex, amphechloral, amphetamine, benzphetamine, chlorphentemine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phenternine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptble salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; Ac: acetyl; THF: tetrahydrofuran; DEAD: diethylazodicarboxylate; DIPEA: N,N-diisopropylethylamine; DMSO: dimethylsulfoxide; EDC: N-(3-Dimethylaminopropyl)-N'-ethylcarbodiimide; HOBT: hydroxybenzotriazole hydrate; Boc: tert-butyloxy carbonyl; Et$_3$N: triethylamine; DCM: dichloromethane; DCE: dichloroethane; BSA: bovine serum albumin; TFA: trifluoracetic acid; DMF: N,N-dimethylformamide; MTBE: methyl tert-butyl ether; SOCl$_2$: thionyl chloride; CDI: carbonyl diimidazole; rt: room temperature; HPLC: high performance liquid chromatography. The compounds of the present invention can be prepared in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

SCHEME A

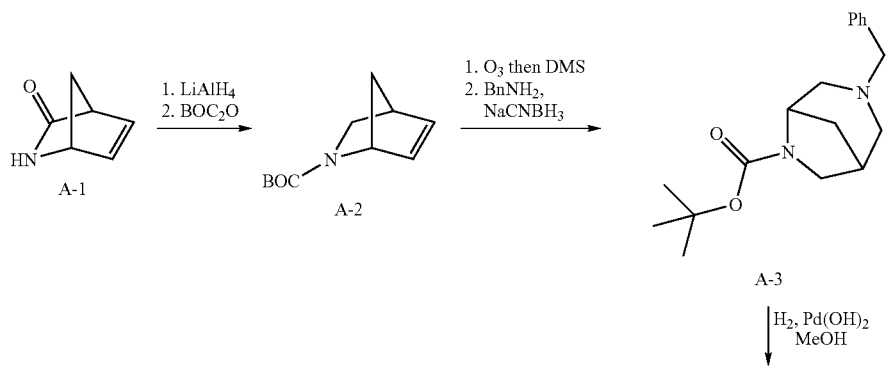

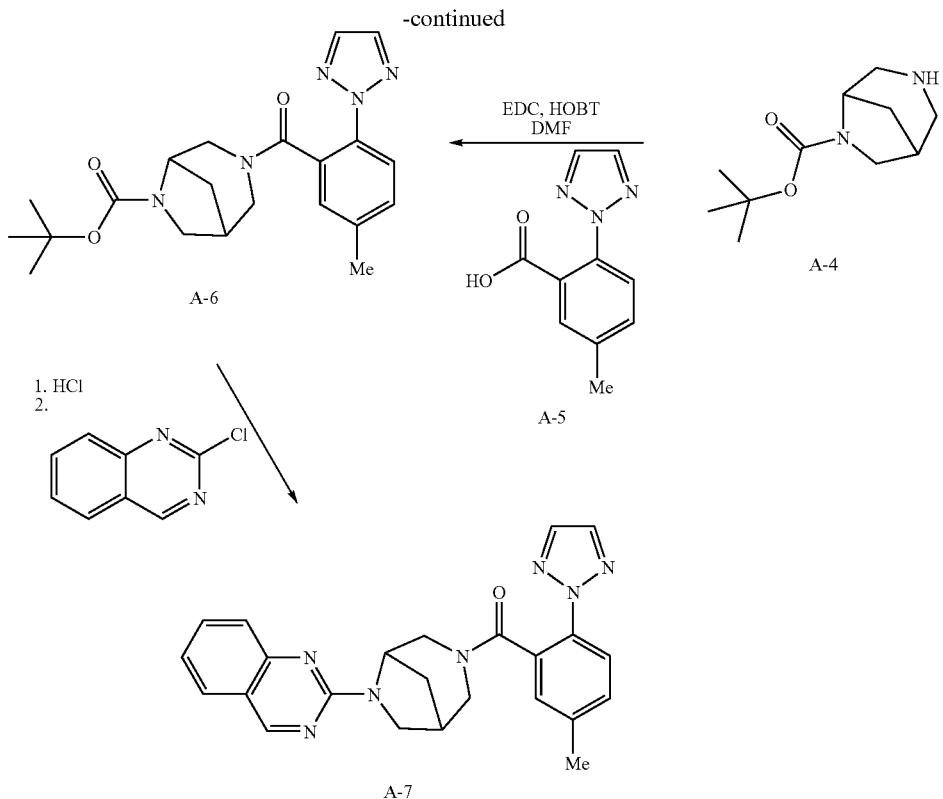

(±) tert-Butyl 2-azabicyclo[2.2.1]hept-5-ene-2-carboxylate (A-2)

A solution of LiAlH$_4$ (800 mL of a 1M soln in THF) was diluted with THF (800 mL) and cooled to 0° C. A solution of racemic 2-azabicyclo[2.2.1]hept-5-en-3-one (Acros; 29 g, 268 mmol) in THF (100 mL) was added via an addition funnel. After the addition was complete, the mixture was stirred for 12 hr at rt and then heated to reflux for 2 hr, cooled to rt, and placed in an ice-bath. The mixture was cautiously quenched with water (31 mL), followed by 15% aq NaOH (31 mL), and then water (93 mL). Solid Na$_2$SO$_4$ and Et$_2$O (1000 mL) were added and the mixture stirred vigorously for 1 hr. The solution was filtered and then treated with Et$_3$N (56.1 mL) and BOC-anhydride (64.4 g, 20.35 mmol). The reaction was stirred for 72 h. The solution was washed with water, satd aq NH$_4$Cl, and brine. The organic solution was dried over MgSO$_4$, filtered and concentrated to provide the desired carbamate A-2 (quantitative yield) as a pale orange oil. Data for A-2: $^1$HNMR (500 MHz, CDCl$_3$) δ Data (2 rotamers; data for major rotamer) 6.28 (br s, 2H), 4.58 (br s, 1H), 3.31 (m, 1H), 3.18 (s, 1H), 2.67-2.55 (m, 1H), 1.46 (br s, 9H) ppm.

(±)-tert-Butyl 3-benzyl-3,6-diazabicyclo[3.2.1]octane-6-carboxylate (A-3)

A solution of the alkene A-2 (52.6 g, 269 mmol) in DCM (2700 mL) was cooled to −78° C. and treated with a steady flow of O$_3$ (g) until a persistent blue color was evident. The reaction was purged with N$_2$ (g) and then treated with DMS (50.2 g, 808 mmol). The solution was warmed to rt and stirred for 24 hr. The reaction was then concentrated to a dark brown oil. A solution of the crude dialdehyde in MeOH (2700 mL) at 0° C. was treated with benzylamine (31.7 g, 296 mmol) and NaCNBH$_3$ (67.7 g, 1077 mmol). The ice-bath was removed and the reaction stirred at rt overnight. In the morning, water was cautiously added, the mixture partially reduced in volume, and the mixture extracted with EtOAc. The organic solution was washed with satd aq NaHCO$_3$, brine, dried over Na$_2$SO$_4$, filtered and concentrated. The residue was purified by flash chromatography (5% EtOAc in CH$_2$Cl$_2$) to afford A-3. Data for A-3: LRMS m/z (M+H) 303.2, found. 303.2 required.

(±)-tert-Butyl 3,6-diazabicyclo[3.2.1]octane-6-carboxylate (A-4)

A solution of the benzyl amine A-3 (24.3 g, 80 mmol) in MeOH (700 Ml) was treated with Pd(OH)$_2$ (4.86 g, 6.92 mmol) and sealed in a 2 L high pressure bomb. The vessel was purged with nitrogen gas and evacuated (three times). The reaction was heated to 65° C. and pressurized with hydrogen gas to 1000 psi. The reaction was stirred at this pressure at 65° C. overnight. The vessel was depressurized and purged with nitrogen gas. The reaction mixture was filtered through celite, the filter cake was washed with EtOAc, and the filtrate concentrated to yield A-4 as a tan oil. Data for A-4: LRMS m/z (M+H) 213.1, found. 213.2 required.

(±) 2-(2H-1,2,3-Triazol-2-yl)-5-methylbenzoic acid (A-5)

A solution of 2-iodo-5-methylbenzoic acid (4.0 g, 15.3 mmol) in DMF (10 mL) was treated with 1,2,3-triazole (2.1 g, 30.5 mmol), CsCO$_3$ (9.95 g, 30.5 mmol), CuI (0.145 g, 0.76 mmol) and trans-N,N'-dimethylcyclohexane-1,2-diamine (0.43 g, 3.05 mmol). The mixture was heated at 120° C. for 10 min in a microwave reactor. The reaction was cooled to room temperature, diluted with water, and washed with EtOAc. The aqueous phase was acidified with 1N HCl and extracted with EtOAc. The organic layer was dried over $Na_2SO_4$, filtered and concentrated. The residue was purified by gradient elution on $SiO_2$ (0 to 10% MeOH in water with 0.1% AcOH) to give the faster eluting 2-(2H-1,2,3-triazol-2-yl)-5-methylbenzoic acid A-5, followed by the undesired regioisomer isomer, 1-(2H-1,2,3-triazol-2-yl)-5-methylbenzoic acid. Data for A-5: $^1$HNMR (500 MHz, DMSO-$d_6$) d 12.98 (br s, 1H), 8.04 (s, 2H), 7.72-7.45 (m, 3H), 2.41 (s, 3H) ppm.

(±) tert-Butyl 3-[5-methyl-2-(2H-1,2,3-triazol-2-yl) benzoyl]-3,6-diazabicyclo[3.2.1]octane-6-carboxylate (A-6)

A solution of the amine A-5 (85 mg, 0.400 mmol) in DMF (4 ml) was treated with aryl acid (89 mg, 0.440 mmol), EDC (115 mg, 0.601 mmol), HOBT (92 mg, 0.601 mmol), and TEA (0.167 ml, 1.201 mmol). After stirring at RT for 1 h 40 min, the mixture was diluted with EtOAc, washed twice with water, sat. aq. $NaHCO_3$, and brine. The organic phase was dried over $Na_2SO_4$, filtered and concentrated to yield A-6 as a colorless film. Data for A-6: LRMS m/z (M+H) 398.0, found. 398.2 required.

(±) 2-{3-[5-methyl-2-(2H-1,2,3-triazol-2-yl)benzoyl]-3,6-diazabicyclo[3.2.1]oct-6-yl}quinazoline (A-7)

A solution of the carbamate A-6 (143 mg, 0.360 mmol) was treated with HCl in dioxane (4M HCl, 4 mL). The reaction was stirred for 15 min at RT and concentrated. A solution of the amine hydrochloride (57 mg, 0.171 mmol) in DMF (2 ml) was treated with 2-chloroquinazoline (28.1 mg, 0.171 mmol) and $K_2CO_3$ (70.8 mg, 0.512 mmol). After stirring for 15 min at 125° C. in a microwave reactor, the mixture was diluted with EtOAc and washed with water. The organic phase was dried over $Na_2SO_4$, filtered and concentrated. The crude material was purified by gradient elution on silica gel (0 to 100% [9:1EtOAc:MeOH] in Hex) to yield A-7 as a yellow oil. Data for A-7 HRMS m/z (M+H), 426.2017 found. 426.2037 required (R,R and S,S)-2-{3-[5-methyl-2-(2H-1,2,3-triazol-2-yl)benzoyl]-3,6-diazabicyclo[3.2.1]oct-6-yl}quinazoline (A-7a and A-7b). The enantiomers of A-7 were resolved by preparative chiral chromatography (ChiralPak AD 2×25 cm column; eluting with 40% hexanes/60% EtOAc). The first eluting enantiomer A-7a has a retention time=14.3 min; the second eluting isomer A-7b has a retention time=17.9 min.

TABLE A

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation.

| Cpd | Structure | Name | HRMS m/z (M + H) |
|---|---|---|---|
| A-8 | 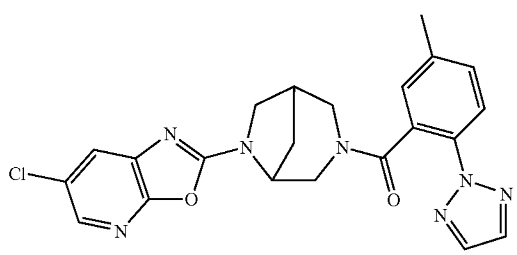 | (±)-6-Chloro-2-{3-[5-methyl-2-(2H-1,2,3-triazol-2-yl)benzoyl]-3,6-diazabicyclo[3.2.1]oct-6-yl}[1,3]oxazolo[5,4-b]pyridine | LRMS m/z (M + H) 452.1 found, 451.13 required. |
| A-9 | 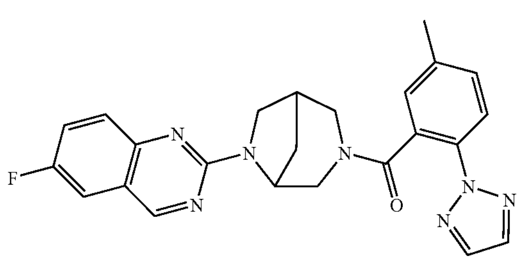 [SMILES: Cc1ccc(-n2nccn2)c(C(=O)N2CC3CC(C2)N(c2ncc4cc(F)ccc4n2)C3)c1] | (±)-6-Fluoro-2-{3-[5-methyl-2-(2H-1,2,3-triazol-2-yl)benzoyl]-3,6-diazabicyclo[3.2.1]oct-6-yl}quinazoline | 444.1941 found, 444.1943 required |
| A-10 | 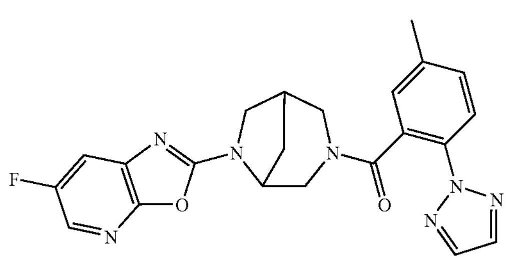 [SMILES: Cc1ccc(-n2nccn2)c(C(=O)N2CC3CC(C2)N(c2nc4cc(F)cnc4o2)C3)c1] | (±)-6-Fluoro-2-{3-[5-methyl-2-(2H-1,2,3-triazol-2-yl)benzoyl]-3,6-diazabicyclo[3.2.1]oct-6-yl}[1,3]oxazolo[5,4-b]pyridine | 434.1719 found, 434.1736 required |

TABLE A-continued

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation.

| Cpd | Structure | Name | HRMS m/z (M + H) |
| --- | --- | --- | --- |
| A-11 | 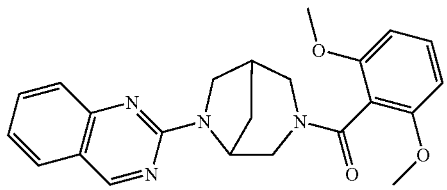 [SMILES: COc1cccc(OC)c1C(=O)N1CC2CC(C1)N(c1ncc3ccccc3n1)C2] | (±)-2-[3-(2,6-Dimethoxybenzoyl)-3,6-diazabicyclo[3.2.1]oct-6-yl]quinazoline | 405.1906 found, 405.1921 required |
| A-12 | 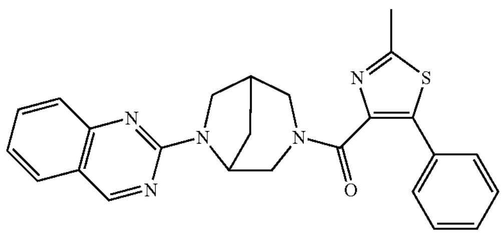 [SMILES: Cc1nc(C(=O)N2CC3CC(C2)N(c2ncc4ccccc4n2)C3)c(-c2ccccc2)s1] | (±)-2-{3-[(2-Methyl-5-phenyl-1,3-thiazol-4-yl)carbonyl]-3,6-diazabicyclo[3.2.1]oct-6-yl}quinazoline | 442.1672 found, 442.1696 required |
| A-13 | 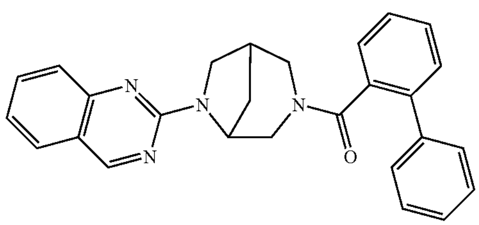 [SMILES: O=C(c1ccccc1-c1ccccc1)N1CC2CC(C1)N(c1ncc3ccccc3n1)C2] | (±)-2-[3-(Biphenyl-2-ylcarbonyl)-3,6-diazabicyclo[3.2.1]oct-6-yl]quinazoline | 421.2007 found, 421.2023 required |
| A-14 | 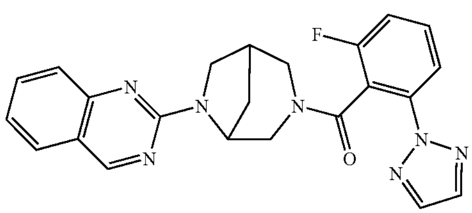 [SMILES: O=C(c1c(F)cccc1-n1nccn1)N1CC2CC(C1)N(c1ncc3ccccc3n1)C2] | 2-{3-[2-Fluoro-6-(2H-1,2,3-triazol-2-yl)benzoyl]-3,6-diazabicyclo[3.2.1]oct-6-yl}quinazoline | 430.1762 found, 430.1792 required |
| A-15 | 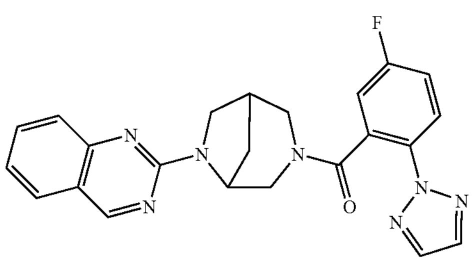 [SMILES: O=C(c1cc(F)ccc1-n1nccn1)N1CC2CC(C1)N(c1ncc3ccccc3n1)C2] | (±)-2-{3-[5-Fluoro-2-(2H-1,2,3-triazol-2-yl)benzoyl]-3,6-diazabicyclo[3.2.1]oct-6-yl}quinazoline | 430.177 found, 430.1786 required |
| A-16 | 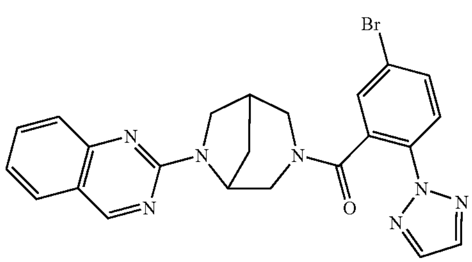 [SMILES: O=C(c1cc(Br)ccc1-n1nccn1)N1CC2CC(C1)N(c1ncc3ccccc3n1)C2] | (±)-2-{3-[5-Bromo-2-(2H-1,2,3-triazol-2-yl)benzoyl]-3,6-diazabicyclo[3.2.1]oct-6-yl}quinazoline | 490.0976 found, 490.0986 required |

TABLE A-continued

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation.

| Cpd | Structure | Name | HRMS m/z (M + H) |
|---|---|---|---|
| A-17 | 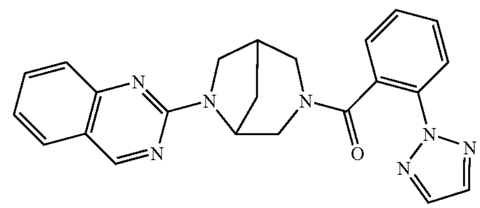 [SMILES: O=C(c1ccccc1-n1nccn1)N1CC2CC(C1)N(c1ncc3ccccc3n1)C2] | (±)-2-{3-[2-(2H-1,2,3-Triazol-2-yl)benzoyl]-3,6-diazabicyclo[3.2.1]oct-6-yl}quinazoline | 412.1852 found, 412.1881 required |
| A-18 | 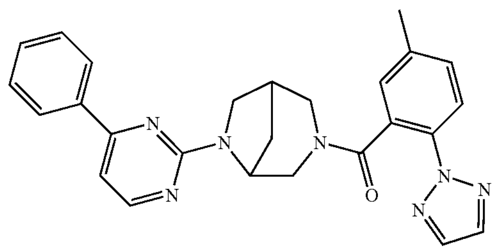 [SMILES: Cc1ccc(-n2nccn2)c(C(=O)N2CC3CC(C2)N(c2nccc(-c4ccccc4)n2)C3)c1] | (±)-3-[5-Methyl-2-(2H-1,2,3-triazol-2-yl)benzoyl]-6-(6-phenylpyrazin-2-yl)-3,6-diazabicyclo[3.2.1]octane | 452.2181 found, 452.2194 required |
| A-19 | 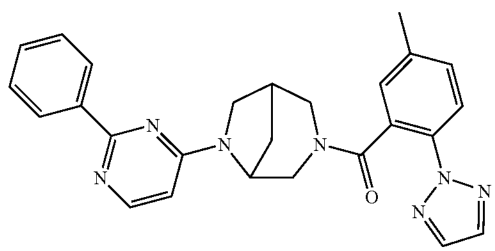 [SMILES: Cc1ccc(-n2nccn2)c(C(=O)N2CC3CC(C2)N(c2ccnc(-c4ccccc4)n2)C3)c1] | (±)-3-[5-Methyl-2-(2H-1,2,3-triazol-2-yl)benzoyl]-6-(2-phenylpyrimidin-4-yl)-3,6-diazabicyclo[3.2.1]octane | 452.218 found, 452.2194 required |
| A-20 | 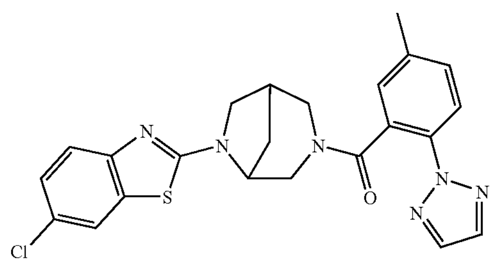 [SMILES: Cc1ccc(-n2nccn2)c(C(=O)N2CC3CC(C2)N(c2nc4ccc(Cl)cc4s2)C3)c1] | (±)-6-Chloro-2-{3-[5-methyl-2-(2H-1,2,3-triazol-2-yl)benzoyl]-3,6-diazabicyclo[3.2.1]oct-6-yl}-1,3-benzothiazole | 465.1235 found, 465.1259 required |
| A-21 | 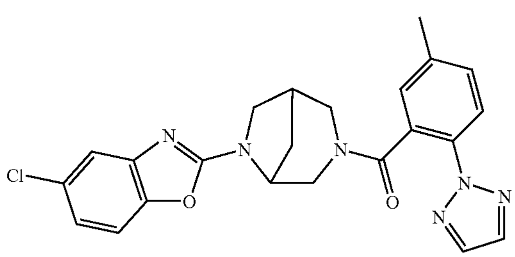 [SMILES: Cc1ccc(-n2nccn2)c(C(=O)N2CC3CC(C2)N(c2nc4cc(Cl)ccc4o2)C3)c1] | (±)-5-chloro-2-{3-[5-methyl-2-(2H-1,2,3-triazol-2-yl)benzoyl]-3,6-diazabicyclo[3.2.1]oct-6-yl}-1,3-benzoxazole | 465.1235 found, 465.1259 required |
| A-22 | 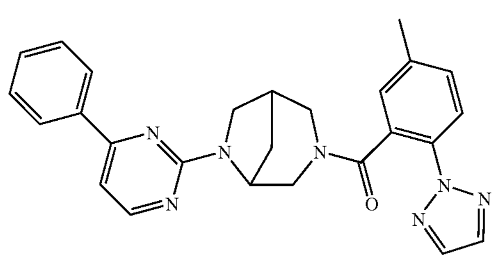 [SMILES: Cc1ccc(-n2nccn2)c(C(=O)N2CC3CC(C2)N(c2nccc(-c4ccccc4)n2)C3)c1] | (±)-3-[5-Methyl-2-(2H-1,2,3-triazol-2-yl)benzoyl]-6-(4-phenylpyrimidin-2-yl)-3,6-diazabicyclo[3.2.1]octane | 452.2179 found, 452.2194 required |

TABLE A-continued

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation.

| Cpd | Structure | Name | HRMS m/z (M + H) |
|---|---|---|---|
| A-23 | 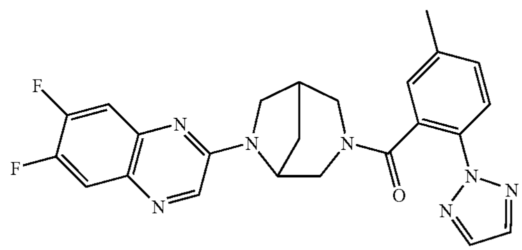 [SMILES: Cc1ccc(-n2nccn2)c(C(=O)N2CC3CC(C2)N(c2cnc4cc(F)c(F)cc4n2)C3)c1] | (±)-6,7-Difluoro-2-{3-[5-methyl-2-(2H-1,2,3-triazol-2-yl)benzoyl]-3,6-diazabicyclo[3.2.1]oct-6-yl}quinoxaline | 462.1831 found, 462.1849 required |
| A-24 | 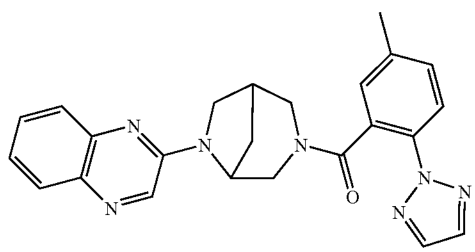 [SMILES: Cc1ccc(-n2nccn2)c(C(=O)N2CC3CC(C2)N(c2cnc4ccccc4n2)C3)c1] | (±)-2-{3-{5-Methyl-2-(2H-1,2,3-triazol-2-yl)benzoyl]-3,6-diazabicyclo[3.2.1]oct-6-yl}quinoxaline | 426.2026 found, 426.2037 required |

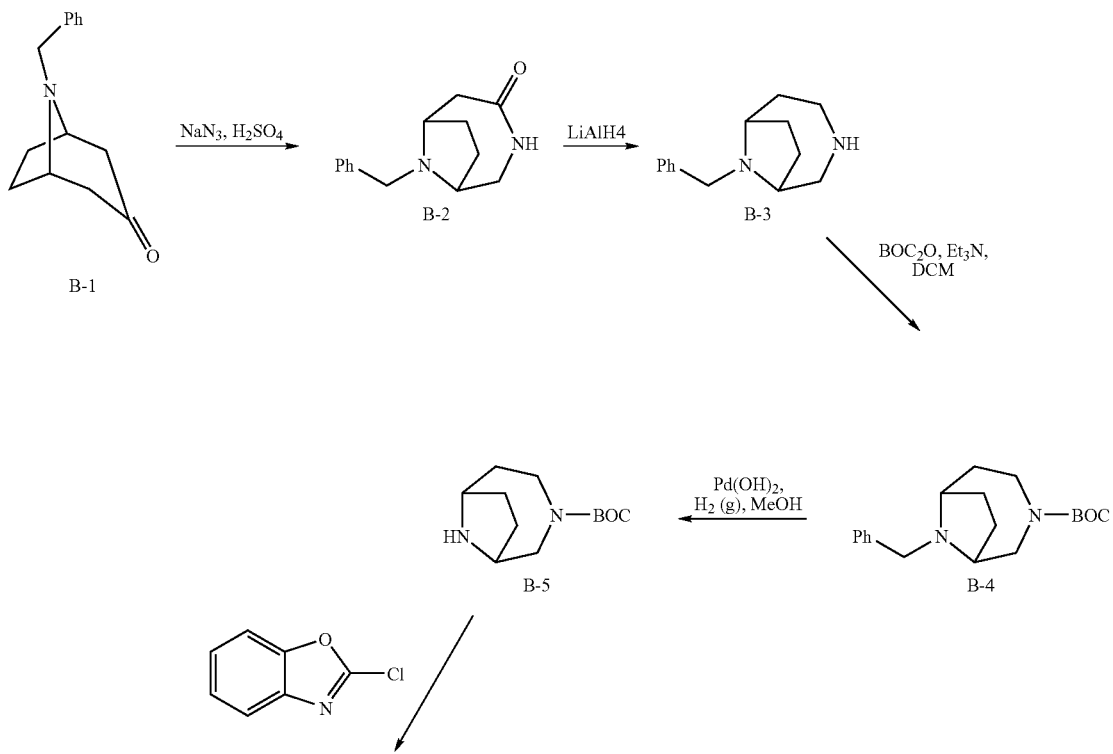

SCHEME B

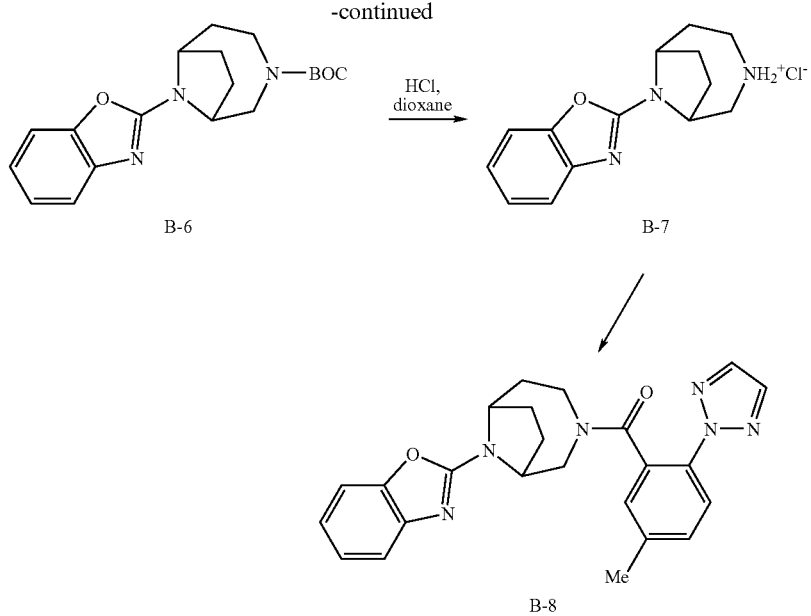

(±)-9-Benzyl-3,9-diazabicyclo[4.2.1]nonan-4-one (B-2)

A cooled solution (−5° C.; ice-salt bath) of the ketone B-1 (5 g, 23.22 mmol) in $CHCl_3$ (50 ml) in a 125 mL erlenmeyer flask was treated dropwise with $H_2SO_4$ (12.38 ml, 232 mmol) keeping the temperature below 15° C. (tan precipitate forms). After cooling to 5° C., the stirred reaction mixture returned to a homogenous state and was treated with $NaN_3$ (3.02 g, 46.4 mmol) in small portions. The temperature did not rise above 5° C. The portionwise addition of the azide resulted in a white precipitate and required about 1 h after which the reaction mixture was stirred at 50° C. in a warm water bath for 1 h (substantial gas evolution). After the mixture cooled to RT, it was transferred to a 500 mL Erlenmeyer flask and ice was added so that it was one third filled and was cooled in an ice bath. Solid $K_2CO_3$ was added portionwise until the mixture was strongly basic. This was followed by 25 mL of a 60% KOH solution. The inorganic salts were removed by filtration and washed with $CHCl_3$. The basic filtrate was extracted 3 times with $CHCl_3$. The organic phase was dried over $Na_2SO_4$, filtered and concentrated to yield B-2 as an off white solid. Data for B-2: LRMS m/z (M+H) 231.1, found. 231.1 required.

(±)-9-Benzyl-3,9-diazabicyclo[4.2.1]nonane (B-3)

A solution of the lactam (4.82 g, 20.93 mmol) in THF (150 ml) was treated slowly with LiAiH4 (53.2 ml of a 1M soln in Et2O, 53.2 mmol). After stirring for 2 days, the mixture was treated dropwise with 2.02 mL of water, 2.02 ml of 15% NaOH, and 6.06 mL of water successively. Sodium sulfate was added to the mixture. After stirring for 1 h, the mixture was filtered through celite and the pad was washed with THF. The filtrate was concentrated to yield B-3 as a tan oil. Data for B-3: LRMS m/z (M+H) 217.1, found. 217.2 required.

(±)-tert-Butyl 9-benzyl-3,9-diazabicyclo[4.2.1]nonane-3-carboxylate (B-4)

A solution of the amine B-3 (4.42 g, 20.43 mmol) in DCM (100 ml) was treated with BOC2O (5.22 ml, 22.48 mmol) and TEA (4.27 ml, 30.6 mmol). After stirring overnight, the mixture was washed with water and the organic phase was dried over Na2SO4, filtered and concentrated to yield B-4 as a tan oil. Data for B-4: LRMS m/z (M+H) 317.1, found. 317.2 required.

(±)-tert-butyl 3,9-diazabicyclo[4.2.1]nonane-3-carboxylate (B-5)

A solution of the diazepane B-4 (6.4 g, 20.23 mmol) in MeOH (100 ml) in a 500 mL Parr bottle was degassed with a stream of $N_{2(g)}$ and treated with $Pd(OH)_2$ on carbon (1.28 g, 9.10 mmol). The suspension was evacuated and backfilled with $N_{2\,(g)}$ three times, then evacuated and backfilled with $H_{2\,(g)}$. The mixture was shaken under a $H_{2\,(g)}$ atmosphere (45 psi) at RT overnight. The mixture was evacuated and backfilled with $N_{2\,(g)}$ three times, filtered through celite and the pad was washed with EtOAc. The filtrate was concentrated to yield B-5 as a tan oil. Data for B-5: LRMS m/z (M+H) 227.1, found. 227.2 required.

(±)-tert-Butyl 9-(1,3-benzoxazol-2-yl)-3,9-diazabicyclo[4.2.1]nonane-3-carboxylate (B-6)

A solution of the amine B-5 (75 mg, 0.331 mmol) in THF (3 ml) was treated with 2-chlorobenzoxazole (0.041 ml, 0.365 mmol) and TEA (0.092 ml, 0.663 mmol). After stirring over the weekend, the mixture was diluted with EtOAc and washed with water and brine. The organic phase was dried over $Na_2SO_4$, filtered and concentrated. The crude material was purified by gradient elution on silica gel (0 to 50% EtOAc in Hex) to yield B-6 as a colorless film. Data for B-6: LRMS m/z (M+H) 344.1, found. 344.2 required.

(±)-2-(3,9-Diazabicyclo[4.2.1]non-9-yl)-1,3-benzoxazole hydrochloride (B-7)

A solution of the carbamate (64.5 mg, 0.188 mmol) in Dioxane (3 ml, 4M HCl) was stirred for 30m. The mixture was concentrated to yield B-7 as a white solid. Data for B-7: LRMS m/z (M+H) 244.1, found. 244.1 required.

(±)-2-{3-[5-Methyl-2-(2H-1,23-triazol-2-yl)benzoyl]-3,9-diazabicyclo[4.2.1]non-9-yl}-1,3-benzoxazole (B-8)

A solution of the amine hydrochloride B-7 (53 mg, 0.189 mmol) in DMF (3 ml) was treated with aryl acid (42.3 mg, 0.208 mmol), EDC (54.5 mg, 0.284 mmol), HOBT (43.5 mg, 0.284 mmol) and TEA (0.132 ml, 0.947 mmol). After stirring overnight at RT, the mixture was diluted with EtOAc, washed with water, sat. aq. NaHCO$_3$, and brine. The organic phase was dried over Na$_2$SO$_4$, filtered and concentrated. The crude material was purified by gradient elution on silica gel (0 to 100% EtOAc in Hex) to yield B-8 as a tan foam. Data for B-8: HRMS m/z (M+H) 429.2023, found. 429.2034 required.

TABLE B

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation.

| Cpd | Structure | Name | HRMS m/z (M + H) |
|---|---|---|---|
| B-9 | 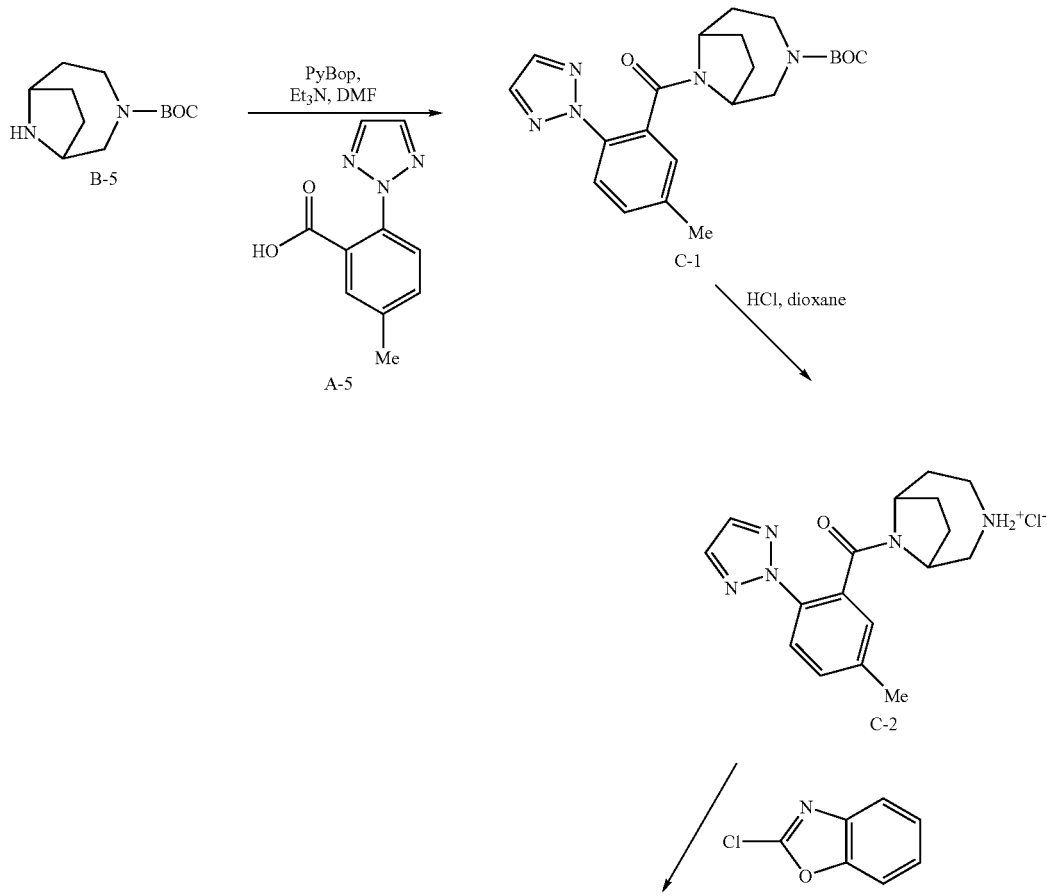 | (±)-2-{3-[5-Methyl-2-(2H-1,2,3-triazol-2-yl)benzoyl]-3,9-diazabicyclo[4.2.1]non-9-yl}quinazoline | 440.2181 found, 440.2194 required. |

SCHEME C

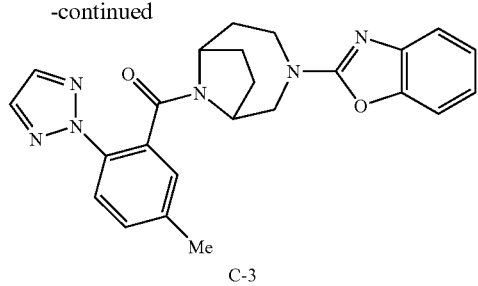

C-3

(±)-tert-Butyl 9-[5-methyl-2-(2H-1,2,3-triazol-2-yl)benzoyl]-3,9-diazabicyclo[4.2.1]nonane-3-carboxylate (C-1)

A solution of the amine B-5 (150 mg, 0.663 mmol) in DMF (3 ml) was treated with aryl acid A-5 (135 mg, 0.663 mmol), PyBOP (379 mg, 0.729 mmol), and TEA (0.185 ml, 1.326 mmol). After stirring for 1 h at room temperature, the mixture was diluted with EtOAc, washed with water, sat. aq. NaHCO$_3$ and brine. The organic phase was dried over Na$_2$SO$_4$, filtered and concentrated. The crude material was purified by gradient elution on silica gel (0 to 60% EtOAc in Hex) to yield C-1 as a colorless film. Data for C-1: LRMS m/z (M+H) 412.0, found. 412.2 required.

(±)-9-[5-Methyl-2-(2H-1,2,3-triazol-2-yl)benzoyl]-3,9-diazabicyclo[4.2.1]nonane hydrochloride (C-2)

A solution of the carbamate (175 Mg, 0.425 Mmol) in dioxane (3 Ml, 4M HCl) was stirred for 30 min. The mixture was concentrated to yield C-2. Data for C-2: LRMS m/z (M+H) 312.1, found. 312.2 required.

(±)-2-{9-[5-Methyl-2-(2H-1,2,3-triazol-2-yl)benzoyl]-3,9-diazabicyclo[4.2.1]non-3-yl}-1,3-benzoxazole (C-3)

A solution of the amine hydrochloride C-2 (74 mg, 0.213 mmol) in DMF (3 ml) was treated with 2-chlorobenzoxazole (0.027 ml, 0.234 mmol) and TEA (0.089 ml, 0.638 mmol). After stirring overnight, the mixture was diluted with EtOAc and washed with water and brine. The organic phase was dried over Na$_2$SO$_4$, filtered and concentrated. The crude material was purified by gradient elution on silica gel (0 to 100% EtOAc in Hex) to yield C-3 as a white foam. Data for C-3: HRMS m/z (M+H) 429.2025, found. 429.2034 required.

TABLE C

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation.

| Cpd | Structure | Name | HRMS m/z (M + H) |
|---|---|---|---|
| C-4 | 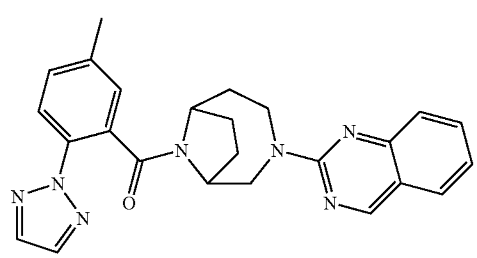 [SMILES: Cc1ccc(-n2nccn2)c(C(=O)N2C3CCC2CN(c2ncc4ccccc4n2)CC3)c1] | (±)-2-{9-[5-Methyl-2-(2H-1,2,3-triazol-2-yl)benzoyl]-3,9-diazabicyclo[4.2.1]non-3-yl}quinazoline | 440.2181 found, 440.2194 required. |
| C-5 | 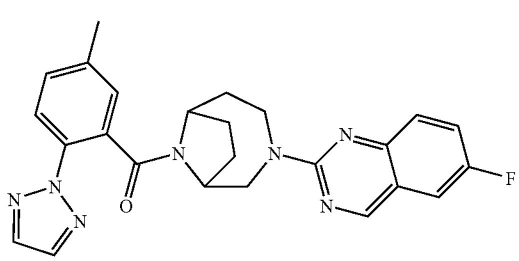 [SMILES: Cc1ccc(-n2nccn2)c(C(=O)N2C3CCC2CN(c2ncc4cc(F)ccc4n2)CC3)c1] | (±)-6-Fluoro-2-{9-[5-methyl-2-(2H-1,2,3-triazol-2-yl)benzoyl]-3,9-diazabicyclo[4.2.1]non-3-yl}quinazoline | 458.209 found, 458.2099 required. |

SCHEME D

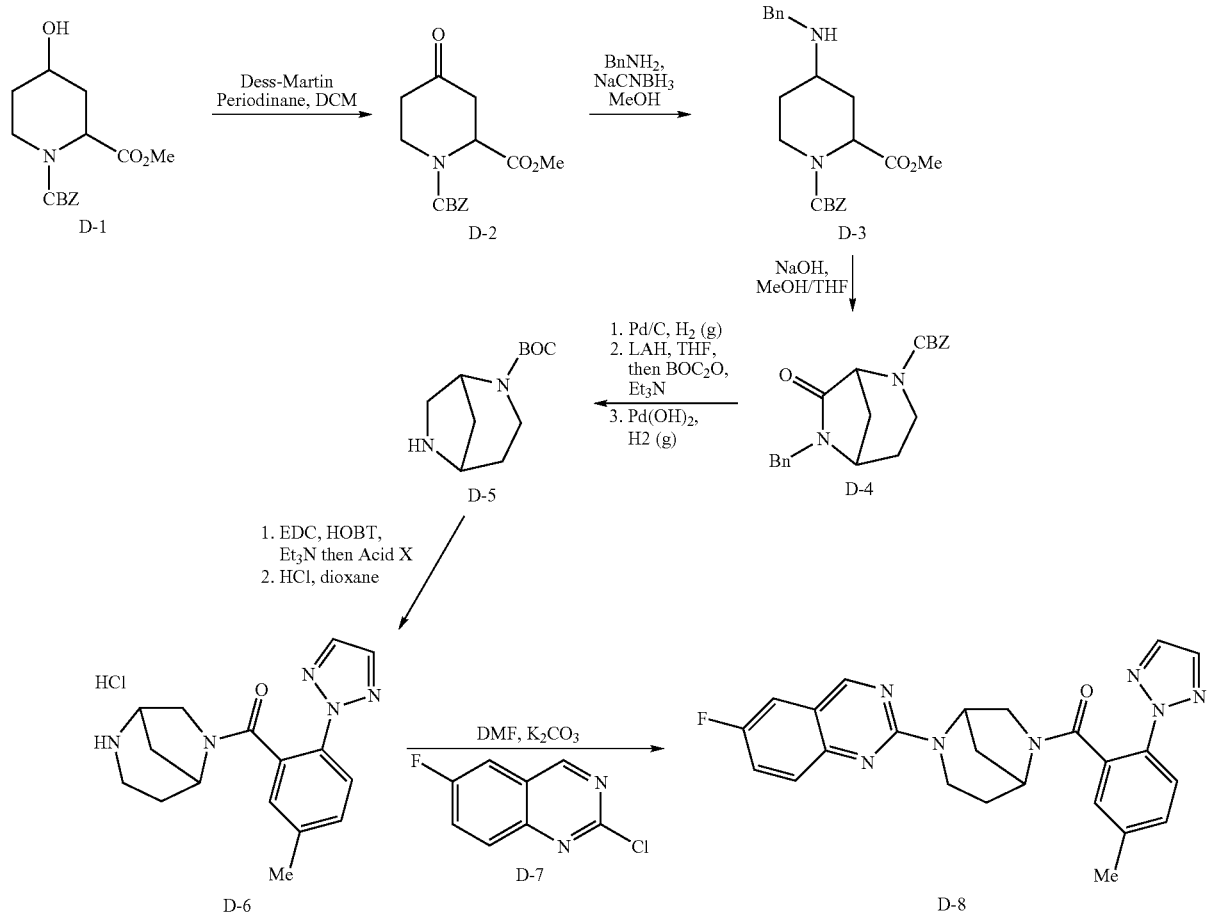

1-Benzyl 2-methyl 4-oxopiperidine-12-dicarboxylate (D-2)

A solution of the alcohol D-1 (500 mg, 1.705 mmol) in DCM (10 ml) was treated with Dess-Martin Periodinane (1085 mg, 2.56 mmol) at RT. After stirring for 4 h, the mixture was treated with sat. aq. Na$_2$S$_2$O$_3$/sat. aq. NaHCO$_3$ (2 mL/2 mL) and stirred for 30 min. The mixture was extracted with DCM and the organic phase was dried over Na$_2$SO$_4$, filtered and concentrated to yield D-2. LRMS m/z (M+H) 292.1, found. 292.3 required.

1-Benzyl-2-methyl-4-(benzylamino)piperidine-1,2-dicarboxylate (D-3)

A solution of the ketone D-2 (484 mg, 1.662 mmol) in MeOH (10 ml) was treated with benzylamine (0.363 ml, 3.32 mmol) and 1 mL of AcOH at RT. After stirring for 1.5 h, the mixture was treated with NaCNBH$_4$ (209 mg, 3.32 mmol) and stirred for 20 min. The mixture was concentrated, dissolved in EtOAc and washed with sat. aq. NaHCO$_3$. The organic phase was dried over Na$_2$SO$_4$, filtered and concentrated to yield D-3. Data for D-3: LRMS m/z (M+H) 383.2, found. 383.5 required.

1-Benzyl-(1S,5R and 1R,5S)-6-benzyl-7-oxo-2,6-diazabicyclo[3.2.1]octane-2-carboxylate (D-4)

A solution of the ester (635 mg, 1.660 mmol) in THF (5 ml)/MeOH (5 ml) was treated with NaOH (199 mg, 4.98 mmol) and 1 mL H$_2$O. After stirring at RT overnight, the mixture was concentrated and partitioned between EtOAc and 1N aq. NaOH. The organic phase was washed with brine, dried over Na$_2$SO$_4$, filtered and concentrated. The crude material was purified by gradient elution on silica gel (0 to 100% EtOAc in Hex) to yield the bicyclic carbamate D-4. LRMS m/z (M+H) 351.2, found. 351.4 required.

tert-Butyl-(1S,5R and 1R,5S)-2,6-diazabicyclo[3.2.1]octane-2-carboxylate (D-5)

A solution of carbamate D4 (207 mg, 0.591 mmol) in MeOH (5 ml) was degassed with a stream of Ar$_{(g)}$ and treated with 10 wt. % Pd(OH)$_2$. The flask was evacuated and back-filled with H2 (g) three times and stirred under a H$_2$ $_{(g)}$ atmosphere (1 atm) at RT for 3 h. The mixture was filtered through a syringe filter and the filtrate was concentrated to yield debenzylated product. A solution of the lactam (128 mg, 0.592 mmol) in THF (5 ml) was treated slowly with LAH (0.654 ml, 1.503 mmol; 1M in Et$_2$O). After stirring for 2 h, the mixture was treated dropwise with 0.057 mL of water, 0.057 ml of 15% NaOH, and 0.171 mL of water successively. Sodium sulfate was added to the mixture. After stirring for 30 min, the mixture was treated with TEA (0.165 ml, 1.184 mmol) and BOC$_2$O (0.165 ml, 0.710 mmol). The mixture was filtered through Celite and the pad was washed with EtOAc. The filtrate was concentrated. The crude material was purified by gradient elution on silica gel (0 to 100% EtOAc in Hex) to yield the amide product. This material (128 mg, 0.423 mmol) was diluted in MeOH (5 ml) and treated with 10 wt. % Pd(OH)$_2$. The flask was evacuated and backfilled with H$_{2\,(g)}$ three times and stirred under a H$_{2\,(g)}$ atmosphere (1 atm) at RT for 1 h. The mixture was filtered through a syringe filter and the filtrate was concentrated to yield D-5. $^1$HNMR (500 MHz, CDCl$_3$) δ 4.75-4.55 (m 1H), 3.95-3.78 (m, 1H), 3.61 (s, 1H), 3.15-2.97 (m, 3H), 2.41 (broad s, 1H), 1.69-1.55 (m, 3H), 1.44 (s, 9H) ppm (1S,5R and 1R,5S)-6-[5-methyl-2-(2H-1,2,3-triazol-2-yl)benzoyl]-2,6-diazabicyclo[3.2.1]octane hydrochloride (D-6)

A solution of the amine D-5 (73 mg, 0.344 mmol) in DMF (2 ml) was treated with aryl acid (77 mg, 0.378 mmol), EDC (99 mg, 0.516 mmol), HOBT (79 mg, 0.516 mmol), and TEA (0.144 ml, 1.032 mmol). After stirring at RT for 1 h 40 min, the mixture was diluted with EtOAc, washed with water and with brine. The organic phase was dried over Na$_2$SO$_4$, filtered and concentrated to yield the amide product. A solution of this product (137 mg, 0.345 mmol) in dioxane/HCl (3 mL, 4M HCl) was stirred at RT for 30 min and the mixture was concentrated to yield D-6. LRMS m/z (M+H) 298.1, found. 298.4 required.

6-Fluoro-2-{(1S,5R and 1R,5S-6-[5-methyl-2-(2H-1,2,3-triazol-2-yl)benzoyl]-2,6-diazabicyclo[3.2.1]oct-2-yl}quinazoline (D-8)

A solution of the amine hydrochloride D-6 (58 mg, 0.174 mmol) in DMF (1 ml) was treated with 2-chloro-6-fluoroquinazoline D-7 (34.9 mg, 0.191 mmol) and K$_2$CO$_3$ (96 mg, 0.695 mmol). After stirring overnight at 65° C., the reaction mixture was diluted with EtOAc and washed twice with water and once with brine. The organic phase was dried over Na$_2$SO$_4$, filtered and concentrated. The crude material was purified by gradient elution on silica gel (0 to 100% EtOAc in Hex) to yield D-8 as a yellow solid. HRMS m/z (M+H) 444.1948, found. 444.1943 required.

TABLE D

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation. Some final products were purified by flash chromatography (SiO$_2$; EtOAc/hexanes) and were isolated as the free-base; alternately, some products were purified by reverse phase HPLC (CH$_3$CN/H$_2$O containing 0.1% TFA as a modifier) and isolated as the TFA salt, in which case the masses reported and found are for the free-base. Alternatively, fractions containing the product could be basified with NaHCO$_3$ and extracted with EtOAc, dried over Na$_2$SO$_4$, and concentrated to provide the free-base.

| Cpd | Structure | Name | HRMS m/z (M + H) |
|---|---|---|---|
| D-9 | 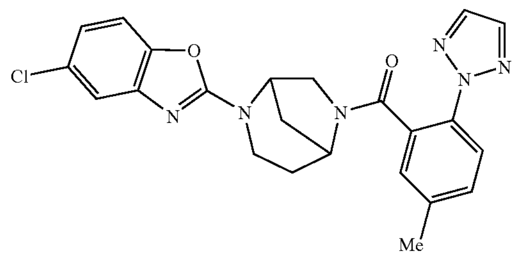 [SMILES: Cc1ccc(-n2nccn2)c(C(=O)N2CC3CC2CCN3c2nc3cc(Cl)ccc3o2)c1] | 5-chloro-2-{(1S,5R and 1R,5S)-6-[5-methyl-2-(2H-1,2,3-triazol-2-yl)benzoyl]-2,6-diazabicyclo[3.2.1]oct-2-yl}-1,3-benzoxazole | 449.1482 found, 449.1488 required. |

SCHEME E

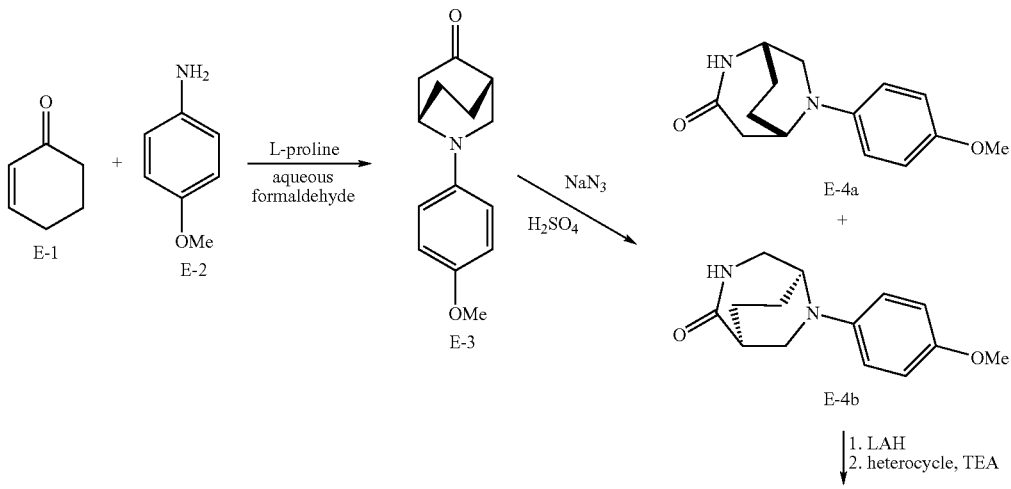

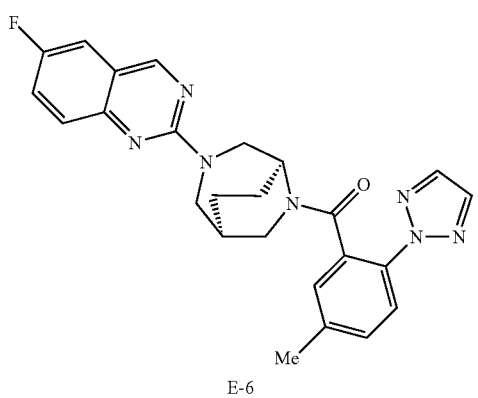

E-6

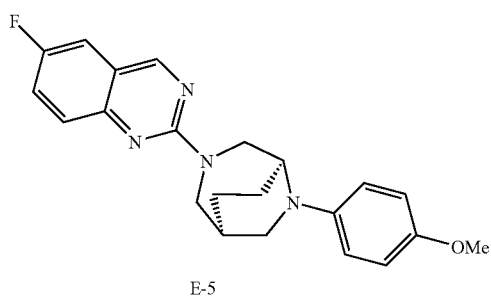

E-5

(1S,4S)-2-(4-methoxyphenyl)-2-azabicyclo[2.2.2]octan-5-one (E-3)

A solution of p-anisidine (E-2, 8.13 g, 66.0 mmol, 1.1 equiv), L-proline (2.07 g, 18.0 mmol, 0.3 equiv), 2-cyclohexen-1-one (E-1, 11.54 g, 120.0 mmol, 2.0 equiv), and 37% aqueous formaldehyde (4.47 mL, 60.0 mmol, 1.0 equiv) was made in DMSO (100 mL) and the reaction was heated to 50° C. for 24 h. The reaction was cooled and diluted with ethyl acetate (500 mL) and washed with water (5×100 mL). The organic phase was dried over MgSO$_4$ and concentrated to an oil. The crude residue was purified by chromatography on silica gel (0 to 80% ethyl acetate in hexanes) to afford the E-3 as a beige solid. $^1$HNMR (500 MHz, CDCl$_3$) δ 6.86 (d, J=9.0 Hz, 2H), 6.64 (d, J=9.0 Hz, 2H), 4.24-4.19 (m, 1H), 3.76 (s, 3H), 3.68-3.63 (m, 1H), 3.48 (d, J=9.5 Hz, 1H), 2.70-2.60 (m, 2H), 2.42 (d, J=18.5 Hz, 1H), 2.22-2.12 (m, 1H), 2.06-1.93 (m, 2H), 1.86-1.78 (m, 1H) ppm; ESI MS [M+H] for C$_{14}$H$_{17}$NO$_2$=232.0.

(1S,5S)-6-(4-methoxyphenyl)-2,6-diazabicyclo[3.2.2]nonan-3-one (E-4a) and (1S,5S)-6-(4-methoxyphenyl)-3,6-diazabicyclo[3.2.2]nonan-2-one (E-4-b)

A solution of (1S,4S)-2-(4-methoxyphenyl)-2-azabicyclo[2.2.2]octan-5-one (E-3, 1.00 g, 4.32 mmol, 1.0 equiv) was made in concentrated sulfuric acid (19.7 mL) at 0° C. and to this was added sodium azide (0.35 g, 5.40 mmol, 1.25 equiv). After 0.5 h, the solution was allowed to warm to ambient temperature. After 2 h, the reaction mixture was made basic using 3N NaOH (300 mL) and the mixture was subsequently extracted with CH$_2$Cl$_2$ (3×200 mL). The organic phase was dried over MgSO$_4$, concentrated, and purified by column chromatography on silica gel (0 to 15% methanol in ethyl acetate) to afford the undesired regioisomer E-4a (more polar) as well as E-4b (less polar) as a white solid. Data for E-4a: $^1$HNMR (500 MHz, CDCl$_3$) δ 7.24-7.18 (m, 1H), 6.85 (d, J=9.0 Hz, 2H), 6.63 (d, J=9.0 Hz, 2H), 4.01 (bs, 1H), 3.76 (s, 3H), 3.65-3.60 (m, 1H), 3.54-3.45 (m, 2H), 3.03-2.96 (m, 1H), 2.64 (dd, J=18.0, 2.5 Hz, 1H), 2.29-2.19 (m, 1H), 2.17-2.08 (m, 1H), 2.03-1.94 (m, 2H) ppm; ESI MS [M+H] for C$_{14}$H$_{18}$N$_2$O$_2$=247.1. Data for E-4-b: $^1$HNMR (500 MHz, CDCl$_3$) δ 6.85 (d, J=9.0 Hz, 2H), 6.66 (d, J=9.0 Hz, 2H), 5.81 (s, 1H), 4.24-4.19 (m, 1H), 3.76 (s, 3H), 3.60-3.53 (m, 2H), 3.42 (d, J=11.0, 4.5 Hz, 1H), 3.29-3.24 (m, 1H), 2.95-2.90 (m, 1H), 2.28-2.20 (m, 1H), 2.16-2.09 (m, 1H), 2.01-1.87 (m, 2H) ppm; ESI MS [M+H] for C$_{14}$H$_{18}$N$_2$O$_2$=247.1.

6-fluoro-2-[(1S,5S)-6-(4-methoxyphenyl)-3,6-diazabicyclo[3.2.2]non-3-yl]quinazoline (E-5)

To a solution of (1S,5S)-6-(4-methoxyphenyl)-3,6-diazabicyclo[3.2.2]-nonan-2-one (E-4, 0.108 g, 0.438 mmol, 1.0 equiv) in THF (3.0 mL) at ambient temperature was added a solution of lithium aluminum hydride in THF (1.31 mL, 1.31 mmol, 1.0M, 3.0 equiv) and the reaction mixture was heated to 65° C. for 2 h. The reaction was cooled to 0° C. and quenched with water (0.1 mL), 1M NaOH (0.2 mL), and water (0.3 mL). The reaction mixture was stirred a further 0.5 h, diluted with ethyl acetate (50 mL), dried over MgSO$_4$, and concentrated to an oil. To a solution of the residual oil in dimethylacetamide (2.1 mL) was added triethylamine (0.24 mL, 1.72 mmol, ca. 4 equiv), and 2-chloro-6-fluoroquinazoline (0.094 g, 0.52 mmol, ca. 1.2 equiv) and the reaction was heated to 175° C. for 15 minutes in the microwave. The reaction was cooled and partitioned between ethyl acetate and water. The organic phase was dried over MgSO$_4$ and concentrated. The residue was purified by column chromatography (0 to 60% ethyl acetate in hexanes) to afford E-5 as a yellow solid. ESI MS [M+H] for C$_{22}$H$_{23}$FN$_4$O=379.2.

6-fluoro-2-{(1R,5S)-6-[5-methyl-2-(2H-1,2,3-triazol-2-yl)benzoyl]-3,6-diazabicyclo[3.2.2]non-3-yl}quinazoline (E-6)

To a solution of 6-fluoro-2-[(1S,5S)-6-(4-methoxyphenyl)-3,6-diazabicyclo[3.2.2]non-3-yl]quinazoline (E-5, 0.020 g, 0.053 mmol, 1.0 equiv) in acetonitrile/water (0.3 mL total; 2:1) at 0° C. was added ceric ammonium nitrate (0.043 g, 0.079 mmol, 1.5 equiv) and the reaction was stirred 1 h. At 1 h, added more ceric ammonium nitrate (0.0 43 g, 0.079 mmol, 1.5 equiv) and the reaction was complete after 2 h. The reaction mixture was quenched with 10% aqueous sodium thiosulfate and concentrated directly. The resulting residue was azeotroped with methanol (2×10 mL) and toluene (2×20 mL). The oily residue was dissolved in DMF (0.3 mL) and to this solution was added EDC (0.030 g, 0.16 mmol, 3.0 equiv), HOBt (0.024 g, 0.16 mmol, 3.0 equiv), triethylamine (0.037 mL, 0.26 mmol, 5.0 equiv), and 2-(2H-1,2,3-triazol-2-yl)-5-methylbenzoic acid (0.032 g, 0.16 mmol, 3.0 equiv). The reaction mixture was heated to 70° C. for 1 h and cooled to ambient temperature. The reaction was partitioned between ethyl acetate (20 mL) and saturated NaHCO$_3$ (20 mL) and the organic phase was washed with water (4×10 mL). The combined organic phase was dried over MgSO4, concentrated and purified by column chromatography on silica gel (0 to 100% ethyl acetate in hexanes). The resulting product was further purified by reverse phase column chromatography (15 to 85% acetonitrile in water, 0.1% TFA buffer) to afford, after free-basing with saturated NaHCO$_3$, E-6 as a yellow foam. HRMS [M+H] C$_{25}$H$_{24}$FN$_7$O calc'd 458.2104, found 458.2115.

TABLE E

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation. Some final products were purified by flash chromatography ($SiO_2$; EtOAc/hexanes) and were isolated as the free-base; alternately, some products were purified by reverse phase HPLC ($CH_3CN/H_2O$ containing 0.1% TFA as a modifier) and isolated as the TFA salt, in which case the masses reported and found are for the free-base. Alternatively, fractions containing the product could be basified with $NaHCO_3$ and extracted with EtOAc, dried over $Na_2SO_4$, and concentrated to provide the free-base.

| Cpd | Structure | Name | HRMS m/z (M + H) |
| --- | --- | --- | --- |
| E-7 | 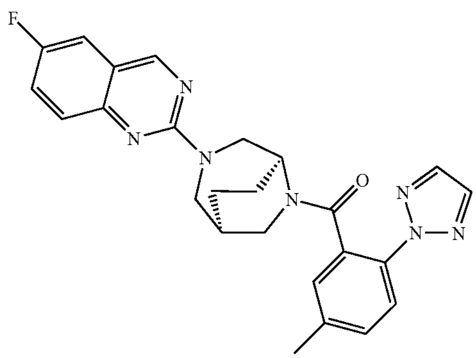 [SMILES: Cc1ccc(-n2nccn2)c(C(=O)N2C[C@@H]3CC[C@H]2CN(c2ncc4cc(F)ccc4n2)C3)c1] | 6-fluoro-2-{(1R,5S)-6-[5-methyl-2-(2H-1,2,3-triazol-2-yl)benzoyl]-3,6-diazabicyclo[3.2.2]non-3-yl}quinazoline | 458.2115 found, 458.2104 required. |

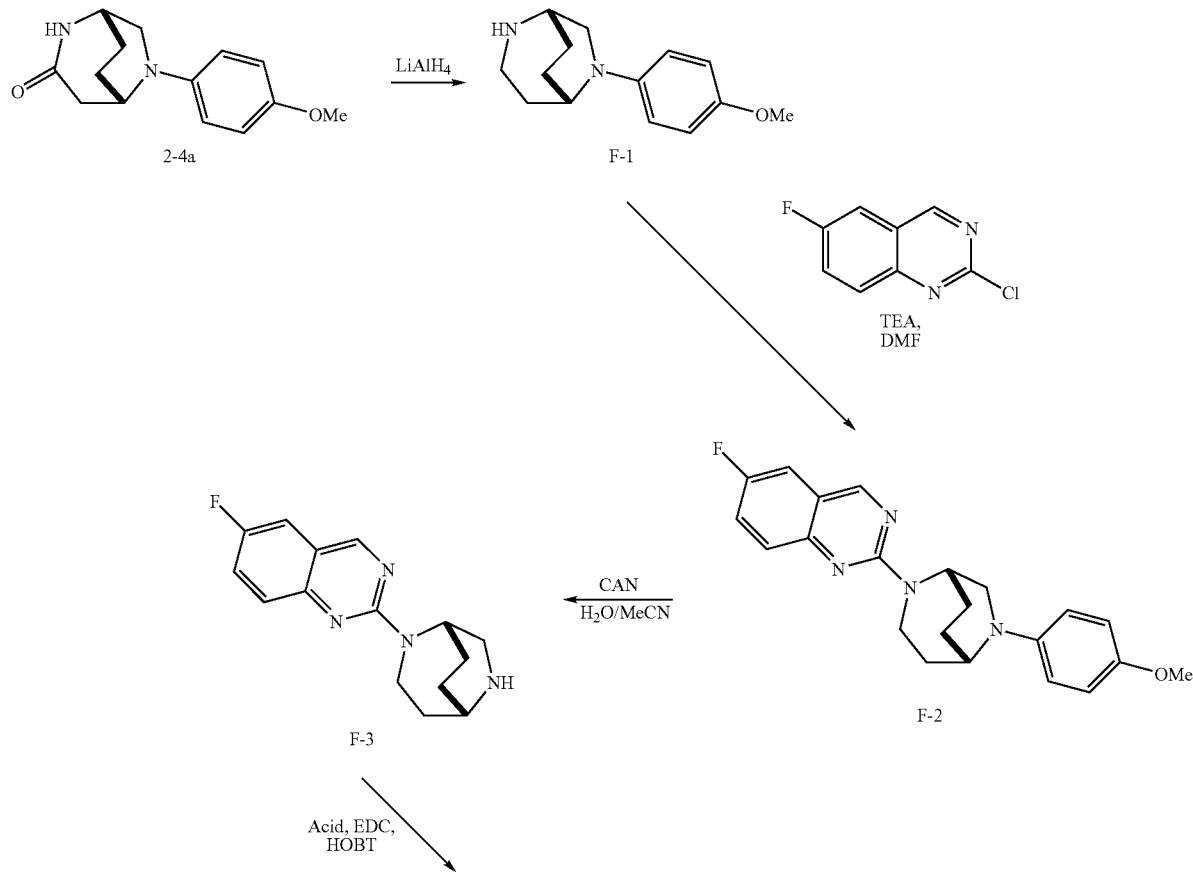

SCHEME F

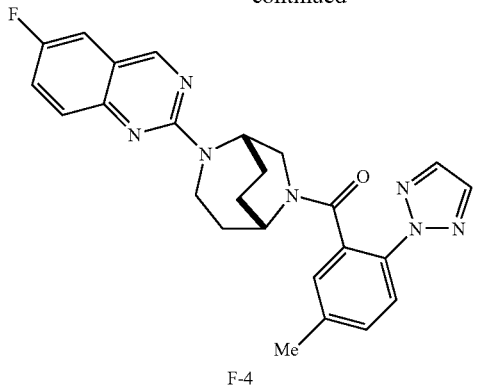

F-4

(1S,5S)-6-(4-Methoxyphenyl)-2,6-diazabicyclo[3.2.2]nonane (F-1)

A suspension of the lactam 2-4-a (300 mg, 1.218 mmol) in THF (10 ml) was treated slowly with LAH (1.589 ml, 3.65 mmol). The solution was heated to reflux and stirred for 1 h, then cooled to 0° C. and treated dropwise with 0.139 mL of water, 0.139 ml of 15% NaOH, and 0.417 mL of water successively. Sodium sulfate was added to the mixture. After stirring for 30 min the mixture was filtered and the filtrate was concentrated to yield F-1 as a tan gum. LRMS m/z (M+H) 233.1, found. 233.32 required.

6-Fluoro-2-[(1S,5S)-6-(4-methoxyphenyl)-2,6-diazabicyclo[3.2.2]non-2-yl]quinazoline (F-2)

A solution of the amine F-1 (147 mg, 0.633 mmol) in DMF (2 ml) was treated with 2-chloro-6-fluoroquinazoline (127 mg, 0.696 mmol) and TEA (0.176 ml, 1.265 mmol). After stirring overnight at 65° C., the reaction mixture was treated with a few drops of 1,1-dimethylethylenediamine to scavenge the excess chloroquinazoline, stirred at 65° C. for 2 additional hours, diluted with EtOAc, washed twice with water and once with brine. The organic phase was dried over $Na_2SO_4$, filtered and concentrated. The crude material was purified by gradient elution on silica gel (0 to 30% EtOAc in Hex) to yield 147 mg of F-2 as a yellow film. LRMS m/z (M+H) 379.2, found. 379.4 required.

2-[(1S,5S)-2,6-Diazabicyclo[3.2.2]non-2-yl]-6-fluoroquinazoline (F-3)

A suspension of the PMP amine, F-2 (147 mg, 0.388 mmol) in acetonitrile (2 ml) and water (1 ml) was cooled to 0° C. and treated with CAN (319 mg, 0.583 mmol) The dark red mixture was stirred for 2 h as it warmed to RT. The solution was treated with an additional 0.5 eq of CAN. After stirring for 30 min, the mixture was quenched with aq. $Na_2S_2O_3$. (turns to a tan solution) The mixture stirred at RT for 72 h and the mixture was concentrated to an aqueous slurry. NaOH (0.5 g) was dissolved in the slurry and it was saturated with NaCl, extracted twice with EtOAc and once with THF. The combined organic phases were dried over $Na_2SO_4$, filtered and concentrated to yield F-3. LRMS m/z (M+H) 273.1, found. 273.3 required.

6-Fluoro-2-{(1S,5S)-6-[5-methyl-2-(2H-1,2,3-triazol-2-yl)benzoyl]-2,6-diazabicyclo[3.2.2]non-2-yl}quinazoline (F-4)

A solution of the amine, F-3 (106 mg, 0.389 mmol) in DMF (4 ml) was treated with aryl acid (79 mg, 0.389 mmol), EDC (82 mg, 0.428 mmol), HOBT (65.6 mg, 0.428 mmol), and TEA (0.163 ml, 1.168 mmol). After stirring at RT for 4 h, the mixture was diluted with EtOAc, washed twice with water, once with sat. aq. $NaHCO_3$ and once with brine. The organic phase was dried over $Na_2SO_4$, filtered and concentrated. The crude material was purified by gradient elution on silica gel (0 to 100% EtOAc in Hex) to yield F-4 as a yellow solid. HRMS m/z (M+H) 458.2089, found. 458.2099 required.

TABLE F

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation. Some final products were purified by flash chromatography (SiO2; EtOAc/hexanes) and were isolated as the free-base; alternately, some products were purified by reverse phase HPLC ($CH_3CN/H_2O$ containing 0.1% TFA as a modifier) and isolated as the TFA salt, in which case the masses reported and found are for the free-base. Alternatively, fractions containing the product could be basified with $NaHCO_3$ and extracted with EtOAc, dried over $Na_2SO_4$, and concentrated to provide the free-base.

| Cpd | Structure | Name | HRMS m/z (M + H) |
|---|---|---|---|
| F-5 | 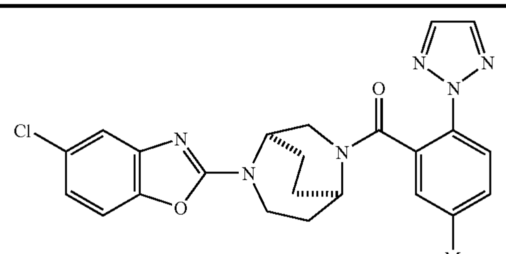 | 5-chloro-2-{(1R,5R)-6-[5-methyl-2-(2H-1,2,3-triazol-2-yl)benzoyl]-2,6-diazabicyclo[3.2.2]non-2-yl}-1,3-benzoxazole | 463.1652 found, 463.1644 required. |

TABLE F-continued

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation. Some final products were purified by flash chromatography (SiO2; EtOAc/hexanes) and were isolated as the free-base; alternately, some products were purified by reverse phase HPLC ($CH_3CN/H_2O$ containing 0.1% TFA as a modifier) and isolated as the TFA salt, in which case the masses reported and found are for the free-base. Alternatively, fractions containing the product could be basified with $NaHCO_3$ and extracted with EtOAc, dried over $Na_2SO_4$, and concentrated to provide the free-base.

| Cpd | Structure | Name | HRMS m/z (M + H) |
| --- | --- | --- | --- |
| F-6 | 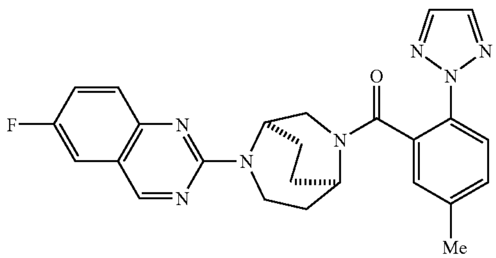 [SMILES: Cc1ccc(-n2nccn2)c(C(=O)N2C[C@H]3CC[C@@H]2CCN3c2ncc3cc(F)ccc3n2)c1] | 6-fluoro-2-{(1R,5R)-6-[5-methyl-2-(2H-1,2,3-triazol-2-yl)benzoyl]-2,6-diazabicyclo[3.2.2]non-2-yl}quinazoline | 458.2096 found, 458.2099 required |
| F-7 | 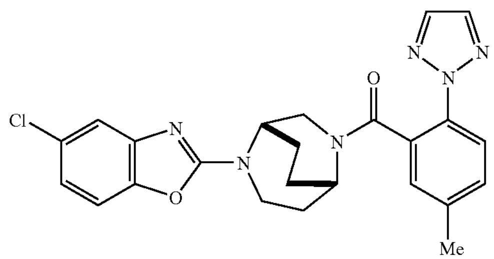 [SMILES: Cc1ccc(-n2nccn2)c(C(=O)N2C[C@@H]3CC[C@H]2CCN3c2nc3cc(Cl)ccc3o2)c1] | 5-chloro-2-{(1S,5S)-6-[5-methyl-2-(2H-1,2,3-triazol-2-yl)benzoyl]-2,6-diazabicyclo[3.2.2]non-2-yl}-1,3-benzoxazole | 463.1653 found, 463.1644 required |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:
1. A compound of the formula I:

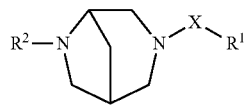

wherein:
X is selected from —$SO_2$—, —(C=O)—, and —(C=S)—;
$R^1$ is selected from the group consisting of:
(1) phenyl, where the phenyl is substituted with $R^{1a}$, $R^{1b}$ and $R^{1c}$,
(2) naphthyl, where the naphthyl is substituted with $R^{1a}$, $R^{1b}$ and $R^{1c}$, and
(3) heteroaryl, where the heteroaryl is substituted with $R^{1a}$, $R^{1b}$ and $R^{1c}$;
$R^2$ is heteroaryl, where the heteroaryl is substituted with $R^{2a}$, $R^{2b}$ and $R^{2c}$;
$R^{1a}$, $R^{1b}$, $R^{1c}$, $R^{2a}$, $R^{2b}$ and $R^{2c}$ are independently selected from the group consisting of:
(1) hydrogen,
(2) halogen,
(3) hydroxyl,
(4) —(C=O)$_m$—O$_n$—$C_{1-6}$alkyl, where m is 0 or 1, n is 0 or 1 (wherein if m is 0 or n is 0, a bond is present) and where the alkyl is unsubstituted or substituted with one or more substituents selected from $R^{13}$,
(5) —(C=O)$_m$—O$_n$—$C_{3-6}$cycloalkyl, where the cycloalkyl is unsubstituted or substituted with one or more substituents selected from $R^{13}$,
(6) —(C=O)$_m$—$C_{2-4}$alkenyl, where the alkenyl is unsubstituted or substituted with one or more substituents selected from $R^{13}$,
(7) —(C=O)$_m$—$C_{2-4}$alkynyl, where the alkynyl is unsubstituted or substituted with one or more substituents selected from $R^{13}$,
(8) —(C=O)$_m$—O$_n$-phenyl or —(C=O)$_m$—O$_n$-naphthyl, where the phenyl or naphthyl is unsubstituted or substituted with one or more substituents selected from $R^{13}$,
(9) —(C=O)$_m$—O$_n$-heterocycle, where the heterocycle is unsubstituted or substituted with one or more substituents selected from $R^{13}$,
(10) —(C=O)$_m$—$NR^{10}R^{11}$, wherein $R^{10}$ and $R^{11}$ are independently selected from the group consisting of:
(a) hydrogen,
(b) $C_{1-6}$alkyl, which is unsubstituted or substituted with one or more substituents selected from $R^{13}$,
(c) $C_{3-6}$alkenyl, which is unsubstituted or substituted with one or more substituents selected from $R^{13}$,
(d) cycloalkyl, which is unsubstituted or substituted with one or more substituents selected from $R^{13}$,
(e) phenyl, which is unsubstituted or substituted with one or more substituents selected from $R^{13}$, and
(f) heterocycle, which is unsubstituted or substituted with one or more substituents selected from $R^{13}$,
(11) —$S(O)_2$—$NR^{10}R^{11}$,

(12) —S(O)$_q$—R$^{12}$, where q is 0, 1 or 2 and where R$^{12}$ is selected from the definitions of R$^{10}$ and R$^{11}$,
(13) —CO$_2$H,
(14) —CN, and
(15) —NO$_2$;
R$^{13}$ is selected from the group consisting of:
(1) halogen,
(2) hydroxyl,
(3) —(C=O)$_m$—O$_n$—C$_{1-6}$alkyl, where the alkyl is unsubstituted or substituted with one or more substituents selected from R$^{14}$,
(4) —O$_n$—(C$_{1-3}$)perfluoroalkyl,
(5) —(C=O)$_m$—O$_n$—C$_{3-6}$cycloalkyl, where the cycloalkyl is unsubstituted or substituted with one or more substituents selected from R$^{14}$,
(6) —(C=O)$_m$—C$_{2-4}$alkenyl, where the alkenyl is unsubstituted or substituted with one or more substituents selected from R$^{14}$,
(7) —(C=O)$_m$—O$_n$-phenyl or —(C=O)$_m$—O$_n$-naphthyl, where the phenyl or naphthyl is unsubstituted or substituted with one or more substituents selected from R$^{14}$,
(8) —(C=O)$_m$—O$_n$-heterocycle, where the heterocycle is unsubstituted or substituted with one or more substituents selected from R$^{14}$,
(9) —CO$_2$H,
(10) —CN, and
(11) —NO$_2$;
R$^{14}$ is selected from the group consisting of:
(1) hydroxyl,
(2) halogen,
(3) C$_{1-6}$alkyl,
(4) —C$_{3-6}$cycloalkyl,
(5) —O—C$_{1-6}$alkyl,
(6) —O(C=O)—C$_{1-6}$alkyl,
(7) —NH—C$_{1-6}$alkyl,
(8) phenyl,
(9) heterocycle,
(10) —CO$_2$H, and
(11) —CN;
or a pharmaceutically acceptable salt thereof.

2. The compound of claim 1 of the formula Ib:

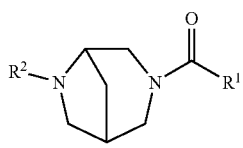

or a pharmaceutically acceptable salt thereof.

3. The compound of claim 1 wherein X is —SO$_2$—.

4. The compound of claim 1 wherein R$^1$ is phenyl, which is unsubstituted or substituted with one or more of:
(1) halogen,
(2) hydroxyl,
(3) —O$_n$—C$_{1-6}$alkyl, where n is 0 or 1 (wherein if n is 0, a bond is present) and where the alkyl is unsubstituted or substituted with one or more substituents selected from R$^{13}$,
(4) —O$_n$-phenyl, where the phenyl is unsubstituted or substituted with one or more substituents selected from R$^{13}$,
(5) -heterocycle, where the heterocycle is unsubstituted or substituted with one or more substituents selected from R$^{13}$,
(6) —NR$^{10}$R$^{11}$, wherein R$^{10}$ and R$^{11}$ are independently selected from the group consisting of:
(a) hydrogen,
(b) C$_{1-6}$alkyl, which is unsubstituted or substituted with one or more substituents selected from R$^{13}$,
(7) —S(O)$_2$—NR$^{10}$R$^{11}$,
(8) —CO$_2$H,
(9) —CN, and
(10) —NO$_2$.

5. The compound of claim 4 wherein R$^1$ is selected from the group consisting of:
(1) phenyl,
(2) biphenyl,
(3) 2,6-dimethoxyphenyl,
(4) 2,4-dichlorophenyl,
(5) 2,6-dichlorophenyl,
(6) 2,3-difluorophenyl,
(7) 2,4-difluorophenyl,
(8) 2,6-difluorophenyl,
(9) 2-methoxy-4-methyl-phenyl,
(10) 3-methoxy-biphenyl,
(11) 3-methyl-biphenyl, and
(12) 5-methyl-2-triazolyl-phenyl.

6. The compound of claim 1 wherein R$^2$ is heteroaryl, which is unsubstituted or substituted with one or more of:
(1) halogen,
(2) hydroxyl,
(3) —O$_n$—C$_{1-6}$alkyl, where n is 0 or 1 (wherein if n is 0, a bond is present) and where the alkyl is unsubstituted or substituted with one or more substituents selected from R$^{13}$,
(4) —O$_n$-phenyl, where the phenyl is unsubstituted or substituted with one or more substituents selected from R$^{13}$,
(5) -heterocycle, where the heterocycle is unsubstituted or substituted with one or more substituents selected from R$^{13}$,
(6) —NR$^{10}$R$^{11}$, wherein R$^{10}$ and R$^{11}$ are independently selected from the group consisting of:
(a) hydrogen,
(b) C$_{1-6}$alkyl, which is unsubstituted or substituted with one or more substituents selected from R$^{13}$,
(7) —S(O)$_2$—NR$^{10}$R$^{11}$,
(8) —CO$_2$H,
(9) —CN, and
(10) —NO$_2$.

7. The compound of claim 5 wherein R$^2$ is selected from the group consisting of:
(1) benzimidazolyl,
(2) benzothiazolyl,
(3) benzoxazolyl,
(4) quinazolinyl,
(5) quinolinyl, and
(6) thiadiazolyl,
which is unsubstituted or substituted with halogen, hydroxyl, C$_{1-6}$alkyl, —O—C$_{1-6}$alkyl or phenyl.

8. A compound which is selected from the group consisting of:
2-{3-[5-Methyl-2-(2H-1,2,3-triazol-2-yl)benzoyl]-3,6-diazabicyclo[3.2.1]oct-6-yl}quinazoline;
(R,R)-2-{3-[5-Methyl-2-(2H-1,2,3-triazol-2-yl)benzoyl]-3,6-diazabicyclo[3.2.1]oct-6-yl}quinazoline;
(S,S)-2-{3-[5-Methyl-2-(2H-1,2,3-triazol-2-yl)benzoyl]-3,6-diazabicyclo[3.2.1]oct-6-yl}quinazoline;
6-Chloro-2-{3-[5-methyl-2-(2H-1,2,3-triazol-2-yl)benzoyl]-3,6-diazabicyclo[3.2.1]oct-6-yl}[1,3]oxazolo[5,4-b]pyridine;

6-Fluoro-2-{3-[5-methyl-2-(2H-1,2,3-triazol-2-yl)benzoyl]-3,6-diazabicyclo[3.2.1]oct-6-yl}quinazoline;
6-Fluoro-2-{3-[5-methyl-2-(2H-1,2,3-triazol-2-yl)benzoyl]-3,6-diazabicyclo[3.2.1]oct-6-yl}[1,3]oxazolo[5,4-b]pyridine;
2-[3-(2,6-Dimethoxybenzoyl)-3,6-diazabicyclo[3.2.1]oct-6-yl]quinazoline;
2-{3-[(2-Methyl-5-phenyl-1,3-thiazol-4-yl)carbonyl]-3,6-diazabicyclo[3.2.1]oct-6-yl}quinazoline;
2-[3-(Biphenyl-2-ylcarbonyl)-3,6-diazabicyclo[3.2.1]oct-6-yl]quinazoline;
2-{3-[2-Fluoro-6-(2H-1,2,3-triazol-2-yl)benzoyl]-3,6-diazabicyclo[3.2.1]oct-6-yl}quinazoline;
2-{3-[5-Fluoro-2-(2H-1,2,3-triazol-2-yl)benzoyl]-3,6-diazabicyclo[3.2.1]oct-6-yl}quinazoline;
2-{3-[5-Bromo-2-(2H-1,2,3-triazol-2-yl)benzoyl]-3,6-diazabicyclo[3.2.1]oct-6-yl}quinazoline;
2-{3-[2-(2H-1,2,3-Triazol-2-yl)benzoyl]-3,6-diazabicyclo[3.2.1]oct-6-yl}quinazoline;
3-[5-Methyl-2-(2H-1,2,3-triazol-2-yl)benzoyl]-6-(6-phenylpyrazin-2-yl)-3,6-diazabicyclo[3.2.1]octane;
3-[5-Methyl-2-(2H-1,2,3-triazol-2-yl)benzoyl]-6-(2-phenylpyrimidin-4-yl)-3,6-diazabicyclo[3.2.1]octane;
6-Chloro-2-{3-[5-methyl-2-(2H-1,2,3-triazol-2-yl)benzoyl]-3,6-diazabicyclo[3.2.1]oct-6-yl}-1,3-benzothiazole;
5-Chloro-2-{3-[5-methyl-2-(2H-1,2,3-triazol-2-yl)benzoyl]-3,6-diazabicyclo[3.2.1]oct-6-yl}-1,3-benzoxazole;
3-[5-Methyl-2-(2H-1,2,3-triazol-2-yl)benzoyl]-6-(4-phenylpyrimidin-2-yl)-3,6-diazabicyclo[3.2.1]octane;
6,7-Difluoro-2-{3-[5-methyl-2-(2H-1,2,3-triazol-2-yl)benzoyl]-3,6-diazabicyclo[3.2.1]oct-6-yl}quinoxaline;
2-{3-[5-Methyl-2-(2H-1,2,3-triazol-2-yl)benzoyl]-3,6-diazabicyclo[3.2.1]oct-6-yl}quinoxaline;
or a pharmaceutically acceptable salt thereof.

9. A pharmaceutical composition which comprises an inert carrier and a compound of claim 1 or a pharmaceutically acceptable salt thereof.

10. A method for enhancing the quality of sleep in a mammalian patient in need thereof which comprises administering to the patient a therapeutically effective amount of the compound of claim 1 or a pharmaceutically acceptable salt thereof.

11. A method for treating insomnia in a mammalian patient in need thereof which comprises administering to the patient a therapeutically effective amount of the compound of claim 1 or a pharmaceutically acceptable salt thereof.

12. A method for treating or controlling obesity in a mammalian patient in need thereof which comprises administering to the patient a therapeutically effective amount of the compound of claim 1 or a pharmaceutically acceptable salt thereof.

* * * * *